(12) United States Patent
Burgess et al.

(10) Patent No.: US 10,300,173 B2
(45) Date of Patent: *May 28, 2019

(54) COMPOUNDS AND METHODS FOR BIOFILM DISRUPTION AND PREVENTION

(71) Applicant: University of Newcastle Upon Tyne, Newcastle Upon Tyne (GB)

(72) Inventors: James Grant Burgess, Newcastle Upon Tyne (GB); Michael John Hall, Newcastle Upon Tyne (GB); Reindert Nijland, Utrecht (NL)

(73) Assignee: University of Newcastle Upon Tyne, Newcastle Upon Tyne (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/586,443

(22) Filed: May 4, 2017

(65) Prior Publication Data

US 2017/0333601 A1    Nov. 23, 2017

Related U.S. Application Data

(62) Division of application No. 13/578,228, filed as application No. PCT/EP2011/052062 on Feb. 11, 2011, now Pat. No. 9,675,736.

(30) Foreign Application Priority Data

Feb. 12, 2010   (GB) .................................. 1002396.8

(51) Int. Cl.
| | | |
|---|---|---|
| *A61K 38/46* | (2006.01) | |
| *A61K 45/06* | (2006.01) | |
| *A61L 29/16* | (2006.01) | |
| *C12N 9/22* | (2006.01) | |

(52) U.S. Cl.
CPC ............ *A61L 29/16* (2013.01); *A61K 38/465* (2013.01); *A61K 45/06* (2013.01); *C12N 9/22* (2013.01); *C12Y 301/31001* (2013.01); *A61L 2300/252* (2013.01); *A61L 2300/30* (2013.01); *A61L 2300/404* (2013.01); *A61L 2300/45* (2013.01); *C12Y 301/27002* (2013.01)

(58) Field of Classification Search
CPC .............. A61K 39/08; A61K 2039/505; A61K 2039/545; A61K 2039/58; A61K 39/40; A61K 45/06; A61K 2039/521; A61K 2039/522; A61K 2039/55566; A61K 39/00; A61K 9/0053; C07K 16/1282; C07K 14/33; C07K 2317/76; C07K 16/40; C07K 2317/12; G01N 2333/33; G01N 33/56911; G01N 2333/32; G01N 2469/10

See application file for complete search history.

(56) References Cited

U.S. PATENT DOCUMENTS

| | | | |
|---|---|---|---|
| 9,675,736 B2 * | 6/2017 | Burgess | ............... A61L 29/16 |
| 2006/0162722 A1 * | 7/2006 | Boehm | ............... A61M 11/06 |
| | | | 128/200.14 |
| 2009/0117642 A1 | 5/2009 | Power et al. | |
| 2009/0130082 A1 | 5/2009 | Kaplan | |
| 2010/0021587 A1 | 1/2010 | Chang et al. | |
| 2010/0075376 A1 | 3/2010 | Rasmussen et al. | |
| 2010/0305062 A1 | 12/2010 | Onsoyen et al. | |

FOREIGN PATENT DOCUMENTS

| | | |
|---|---|---|
| DE | 10304331 A1 | 8/2004 |
| DE | 102005028295 A1 | 11/2006 |
| WO | 2001098214 A1 | 12/2001 |
| WO | 2004108757 A1 | 12/2004 |
| WO | 2006/017816 A2 | 2/2006 |
| WO | 2006031554 A1 | 3/2006 |
| WO | 2006032477 A1 | 3/2006 |
| WO | 2009/121183 A1 | 8/2009 |

OTHER PUBLICATIONS

Pfeffer-Hennig et al. Adv. Exp. Med. Biol. 379: 29-41, 1996.*
Belton et al. J. Gen. Microbiol. 3: 400-409, 1949.*
Lazar et al. Mol. Cellular Biol. 8: 1247-1252, 1988.*
Skolnick et al. Trends in Biotechnology 18: 34-39, 2000.*
Cleton-Jansen et al. Mol. Gen. Genet. 229: 206-212, 1991.*
Ando, et al., J. Biochem., vol. 139, pp. 805-811 (2006).
Costerton, et al., Annu. Rev. Microbiol., vol. 49, pp. 711-745 (1995).
Gristina, et al., JAMA, vol. 259, No. 6, pp. 870-874 (1988).
Maira-Litran, et al., Journal of Applied Microbiology, vol. 88, pp. 243-247 (2000).
Satuito, et al., Hydrobiologia, vol. 358, pp. 275-280 (1997).
Schaik, et al., Journal of Bacteriology, vol. 187, No. 4, pp. 1455-1464 (2005).
Stewart, et al., Antimicrobial Agents and Chemotherapy, vol. 38, No. 5, pp. 1052-1058 (1994).
Vilain, et al., Applied and Environmental Microbiology, vol. 75, No. 9, pp. 2861-2868 (2009).
Sinderen, et al., Mol. Microbiol. 15: 213-223, 1995.
Shaeffer, et al., PNAS 54: 704-711, 1965.
Akrigg, et al., Biochem. J. 172: 63-67, 1978.
International Application Serial No. PCT/EP2011/052062, International Search Report dated Jul. 26, 2011, 6 pgs.
International Application Serial No. PCT/EP2011/052062, Written Opinion dated Jul. 26, 2011, 7 pgs.

(Continued)

*Primary Examiner* — Sarvamangala Devi

(74) *Attorney, Agent, or Firm* — Nevrivy Patent Law Group P.L.L.C.

(57) ABSTRACT

The invention relates to compounds, compositions and methods for biofilm disruption and prevention. In particular, the invention relates to pharmaceutical compositions for the disruption of biofilm and prevention of biofilm in patients. The invention also relates to anti-biofouling compositions for the disruption of biofilm and prevention of biofilm on surfaces. The invention also relates to the removal of biological material from surfaces. The compositions of the invention include microbial deoxyribonucleases.

21 Claims, 13 Drawing Sheets

Specification includes a Sequence Listing.

(56) References Cited

OTHER PUBLICATIONS

Modiya, et al., Org. Med. Chem. Lett. 2(1): Aug. 2012.
Tao, et al., ACS Comb. Sci. 15: 447-451, 2013.
Yan, et al., Applied Environ. Microbiol. 69: 3719-3727, 2003.
Eckart, et al., "DNase1L2 suppresses biofilm formation by pseudomonas aeruginosa and *Staphylococcus aureus*," British Journal of Dermatology (2007) 156: 1342-1345.
Light, et al., "The in vitro efficacy of varidase versus streptokinase or urokinase for liquefying thick purulent exudative material from loculated empyema," Lung (2000) 178: 13-18.
Nemoto, et al., "Effect of varidase (stretodornase) on biofilm formed by pseudomonas aeruginosa," Chemotherapy (2003) 49: 121-125.
Tetz, et al., "Effect of DNase and antibiotics on biofilm characteristics," Antimicrobial Agents and Chemotherapy (2009) 53 (3): 1204-1209.
Whitchurch et al., "Extracellular DNA required for bacterial biofilm formation," Science (2002) 295: 1487.
Zhu, et al., "Tissue plaminogen activator combined with human recombinant deoxyribonuclease is effective therapy for empyema in a rabbit model," Chest (2006) 129: 1577-1583.

* cited by examiner

FIG. 4

Homology Block  Percent Matches 97  Score 269  Length 142

Sequence View. Difference Format, Color behind non-matches

```
MucB (DSM13)    1  MIKKMAVHLLFSALVLLGLSGGAAYSFQHAEGAARYDD LYPPASRYPETQAHISDAIKA
nucB (EI-34-    1  ............................................................

MucB (DSM13)   61  GHS DVCTIEFSGADKFQESLKGIPTKPGFDRQEWPKANCEEGGKGASYRYYSSSDMRGA
nucB (EI-34-   61  ...  ......................................................

MucB (DSM13)  121  GSWVGMRL G ADGTRILFIVQ
nucB (EI-34-  121  .........  M W..........
```

ATGATCAAAAAATGGGCGGTTCATCTGCTGTTTTCCGCATTGGTGCTGCTTGGGCTTTCGGG
AGGGGCTGCATATTCTCCTCAGCATGCCGAAGGCGCTGCAAGGTATGATGACGTATTGTATT
TTCCGGCATCGCGCTATCCTGAAACCGGCGCTCATATAAGCGACGCGATCAAAGCGGGCCAT
GCAGATGTCTGCACAATTGAAAGATCGGGAGCGGATAAGCGCCGTCAGGAATCATTAAAGGG
GATTCCGACCAAGCCGGGCTTTGACCGTGACGAATGGCCGATGGCCATGTGTGAAGAAGGGG
GAAAAGGAGCGTCGGTCAGATATGTCAGCTCATCGGATAACCGCGGAGCCGGTTCCTGGGTC
GGGAACAGGCTGAACGGTTACGCTGACGGGACGAGAATTTTGTTTATCGTTCAATAA

FIG. 6

ATGATCAAAAAATGGGCGGTTCATCTGCTGTTTTCCGCATTGGTACTGCTTGGGCTTTCGGG
AGGCGCCGCATATTCTCCTCAGCATGCCGAAGGTGCTGCAAGGTATGACGACATATTGTATT
TTCCGGCATCACGCTATCCCGAAACCGGCGCTCATATCAGCGACGCAATCAAAGCAGGGCAT
TCAGATGTCTGCACGATTGAAAGATCGGGAGCGGATAAGCGCCGCCAGGAATCACTGAAGGG
GATTCCGACTAAGCCGGGCTTTGACCGTGACGAATGGCCGATGGCCATGTGTGAAGAAGGGG
GCAAAGGAGCGTCTGTCAGATATGTCAGCTCATCGGATAACCGCGGAGCCGGCTCCTGGGTC
GGGAACAGGCTGAGCGGTTTCGCCGACGGGACGAGAATTTTGTTTATCGTTCAATAA

FIG. 7

MIKKWAVHLLFSALVLLGLSGGAAYSPQHAEGAARYDDVLYFPASRYPETGAHISDAIKAGH
ADVCTIERSGADKRRQESLKGIPTKPGFDRDEWPMAMCEEGGKGASVRYVSSSDNRGAGSWV
GNRLNGYADGTRILFIVQ

FIG. 8

ARYDDVLYFPASRYPETGAHISDAIKAGHADVCTIERSGADKRRQESLKGIPTKPGFDRDEW
PMAMCEEGGKGASVRYVSSSDNRGAGSWVGNRLNGYADGTRILFIVQ

FIG. 9

MIKKWAVHLLFSALVLLGLSGGAAYSPQHAEGAARYDDILYFPASRYPETGAHISDAIKAGH
SDVCTIERSGADKRRQESLKGIPTKPGFDRDEWPMAMCEEGGKGASVRYVSSSDNRGAGSWV
GNRLSGFADGTRILFIVQ

FIG. 10

SEQUENCE LISTING

<160> NUMBER OF SEQ ID NOS: 7

<210> SEQ ID NO 1
<211> LENGTH: 429
<212> TYPE: DNA
<213> ORGANISM: Bacillus licheniformis

<400> SEQUENCE: 1

| | | | | | | |
|---|---|---|---|---|---|---|
| atgatcaaaa | aatgggcggt | tcatctgctg | ttttccgcat | tggtgctgct | tgggctttcg | 60 |
| ggagggctg | catattctcc | tcagcatgcc | gaaggcgctg | caaggtatga | tgacgtattg | 120 |
| tattttccgg | catcgcgcta | tcctgaaacc | ggcgctcata | taagcgacgc | gatcaaagcg | 180 |
| ggccatgcag | atgtctgcac | aattgaaaga | tcgggagcgg | ataagcgccg | tcaggaatca | 240 |
| ttaaaggga | ttccgaccaa | gccgggcttt | gaccgtgacg | aatggccgat | ggccatgtgt | 300 |
| gaagaagggg | gaaaaggagc | gtcggtcaga | tatgtcagct | catcggataa | ccgcggagcc | 360 |
| ggttcctggg | tcgggaacag | gctgaacggt | tacgctgacg | ggacgagaat | tttgtttatc | 420 |
| gttcaataa | | | | | | 429 |

<210> SEQ ID NO 2
<211> LENGTH: 429
<212> TYPE: DNA
<213> ORGANISM: Bacillus licheniformis

<400> SEQUENCE: 2

| | | | | | | |
|---|---|---|---|---|---|---|
| atgatcaaaa | aatgggcggt | tcatctgctg | ttttccgcat | tggtactgct | tgggctttcg | 60 |
| ggaggcgccg | catattctcc | tcagcatgcc | gaaggtgctg | caaggtatga | cgacatattg | 120 |
| tattttccgg | catcacgcta | tcccgaaacc | ggcgctcata | tcagcgacgc | aatcaaagca | 180 |
| gggcattcag | atgtctgcac | gattgaaaga | tcgggagcgg | ataagcgccg | ccaggaatca | 240 |
| ctgaagggga | ttccgactaa | gccgggcttt | gaccgtgacg | aatggccgat | ggccatgtgt | 300 |
| gaagaagggg | gcaaaggagc | gtctgtcaga | tatgtcagct | catcggataa | ccgcggagcc | 360 |
| ggctcctggg | tcgggaacag | gctgagcggt | ttcgccgacg | ggacgagaat | tttgtttatc | 420 |
| gttcaataa | | | | | | 429 |

<210> SEQ ID NO 3
<211> LENGTH: 142
<212> TYPE: PRT
<213> ORGANISM: Bacillus licheniformis

<400> SEQUENCE: 3

Met Ile Lys Lys Trp Ala Val His Leu Leu Phe Ser Ala Leu Val Leu
1               5                   10                  15

Leu Gly Leu Ser Gly Gly Ala Ala Tyr Ser Pro Gln His Ala Glu Gly
                20                  25                  30

Ala Ala Arg Tyr Asp Asp Val Leu Tyr Phe Pro Ala Ser Arg Tyr Pro
            35                  40                  45

Glu Thr Gly Ala His Ile Ser Asp Ala Ile Lys Ala Gly His Ala Asp
        50                  55                  60

Val Cys Thr Ile Glu Arg Ser Gly Ala Asp Lys Arg Arg Gln Glu Ser
65                  70                  75                  80

Leu Lys Gly Ile Pro Thr Lys Pro Gly Phe Asp Arg Asp Glu Trp Pro

```
                85                  90                  95
Met Ala Met Cys Glu Glu Gly Gly Lys Gly Ala Ser Val Arg Tyr Val
            100                 105                 110

Ser Ser Ser Asp Asn Arg Gly Ala Gly Ser Trp Val Gly Asn Arg Leu
        115                 120                 125

Asn Gly Tyr Ala Asp Gly Thr Arg Ile Leu Phe Ile Val Gln
    130                 135                 140

<210> SEQ ID NO 4
<211> LENGTH: 109
<212> TYPE: PRT
<213> ORGANISM: Bacillus licheniformis

<400> SEQUENCE: 4

Ala Arg Tyr Asp Asp Val Leu Tyr Phe Pro Ala Ser Arg Tyr Pro Glu
1               5                   10                  15

Thr Gly Ala His Ile Ser Asp Ala Ile Lys Ala Gly His Ala Asp Val
            20                  25                  30

Cys Thr Ile Glu Arg Ser Gly Ala Asp Lys Arg Gln Glu Ser Leu
        35                  40                  45

Lys Gly Ile Pro Thr Lys Pro Gly Phe Asp Arg Asp Glu Trp Pro Met
50                  55                  60

Ala Met Cys Glu Glu Gly Gly Lys Gly Ala Ser Val Arg Tyr Val Ser
65                  70                  75                  80

Ser Ser Asp Asn Arg Gly Ala Gly Ser Trp Val Gly Asn Arg Leu Asn
                85                  90                  95

Gly Tyr Ala Asp Gly Thr Arg Ile Leu Phe Ile Val Gln
            100                 105

<210> SEQ ID NO 5
<211> LENGTH: 142
<212> TYPE: PRT
<213> ORGANISM: Bacillus licheniformis

<400> SEQUENCE: 5

Met Ile Lys Lys Trp Ala Val His Leu Leu Phe Ser Ala Leu Val Leu
1               5                   10                  15

Leu Gly Leu Ser Gly Gly Ala Ala Tyr Ser Pro Gln His Ala Glu Gly
            20                  25                  30

Ala Ala Arg Tyr Asp Asp Ile Leu Tyr Phe Pro Ala Ser Arg Tyr Pro
        35                  40                  45

Glu Thr Gly Ala His Ile Ser Asp Ala Ile Lys Ala Gly His Ser Asp
    50                  55                  60

Val Cys Thr Ile Glu Arg Ser Gly Ala Asp Lys Arg Gln Glu Ser
65                  70                  75                  80

Leu Lys Gly Ile Pro Thr Lys Pro Gly Phe Asp Arg Asp Glu Trp Pro
                85                  90                  95

Met Ala Met Cys Glu Glu Gly Gly Lys Gly Ala Ser Val Arg Tyr Val
            100                 105                 110

Ser Ser Ser Asp Asn Arg Gly Ala Gly Ser Trp Val Gly Asn Arg Leu
        115                 120                 125

Ser Gly Phe Ala Asp Gly Thr Arg Ile Leu Phe Ile Val Gln
    130                 135                 140

<210> SEQ ID NO 6
<211> LENGTH: 41
<212> TYPE: DNA
```

```
<213> ORGANISM: Bacillus licheniformis

<400> SEQUENCE: 6
ataggtgacc gtcatgatca aaaaatgggc ggttcatctg c                    41

<210> SEQ ID NO 7
<211> LENGTH: 32
<212> TYPE: DNA
<213> ORGANISM: Bacillus licheniformis

<400> SEQUENCE: 7
atctctagat atttgttttt cgccttttat tg                              32
```

COMPOUNDS AND METHODS FOR BIOFILM DISRUPTION AND PREVENTION

RELATED APPLICATIONS

This application is a divisional of U.S. application Ser. No. 13/578,228, filed Oct. 31, 2012, which is a US National stage entry of International Application No. PCT/EP2011/052062, which designated the United States and was filed on Feb. 11, 2011, published in English.

This application claims priority under 35 U.S.C. § 119 or 365 to United Kingdom, Application No. 1002396.8, filed Feb. 12, 2010. The entire teachings of the above application(s) are incorporated herein by reference.

FIELD OF THE INVENTION

This invention relates to compositions and methods for biofilm disruption and prevention. The invention relates to pharmaceutical compositions and methods for the disruption of biofilm and the prevention of biofilm in patients. The invention also relates to anti-biofouling compositions and methods for the disruption of biofilm and prevention of biofilm on surfaces. The invention also relates to the removal of biological material from surfaces.

BACKGROUND

Microorganisms generally live attached to surfaces in many natural, industrial, and medical environments, encapsulated by extracellular substances including biopolymers and macromolecules. The resulting layer of slime encapsulated microorganism is termed a biofilm. Biofilms are the predominant mode of growth of bacteria in the natural environment, and bacteria growing in biofilms exhibit distinct physiological properties. Compared to their planktonically grown counterparts, the bacteria in a biofilm are more resistant to antibiotics, UV irradiation, detergents and the host immune response (Gristina et al. 1988. Journal of the American Medical Association, 259: 870-874; Stewart. 1994. Antimicrobial Agents & Chemotherapy, 38(5): 1052-1058; Costerton et al. 1995. Annu. Rev. Microbiol., 49: 711-745; Maira-Litran et al. 2000. Journal of Applied Microbiology, 88: 243-247). A biofilm may include one or more microorganisms, including gram-positive and gram-negative bacteria, algae, protozoa, and/or yeast or filamentous fungi and viruses and/or bacteriophage. Examples of problematic biofilms are dental plaque, infections on medical implants, but also the initial fouling on ship hulls (Satuito et al. 1997. Hydrobiologia, 358: 275-280). Biofilms are attributed to the pathogenesis of many infections in humans and are a significant problem in industry in terms of biofouling of exposed surfaces where biofilm colonisation can form the base component of a localised ecosystem which can disrupt and interfere with industrial processes and components. New strategies are required to inhibit biofilm formation, disperse existing biofilm and to trigger bacteria in a biofilm to return to the antibiotic-sensitive planktonic state.

Many types of microbes grow naturally in a biofilm context, such as bacteria, fungi, algae etc.

It is known in the art that biofilms can have, as a component, DNA (termed extracellular DNA or eDNA) although its function there, remains unknown. Certain groups have sought to employ nuclease enzymes to disrupt biofilms. However, the prior art use of nucleases in this respect has been limited to human DNase and DNase I, an enzyme purified from bovine pancreas and sold commercially.

For instance, WO 06/017816 discloses compositions and methods for the inhibition of biofilm formation or reduction of existing or developing biofilms in a patient. The methods include administering to a subject that has or is at risk of developing biofilms a compound or formulation that inhibits the formation or polymerization of actin microfilaments or depolymerizes actin microfilaments at or proximal to the site of biofilm formation. Such a compound can be administered in combination with a compound or formulation that inhibits the accumulation or activity of cells that are likely to undergo necrosis at or proximal to the site of biofilm formation (i.e., neutrophils). The methods and compositions can further include the use of anti-DNA and/or anti-mucin compounds.

WO 2009/121183 discloses an anti-biofilm composition comprising two or more agents selected from the group consisting of DISPERSIN B, 5-Fluorouracil, Deoxyribonuclease I (bovine DNase I) and Proteinase K for preventing growth and proliferation of biofilm-embedded microorganisms.

Prior art studies have demonstrated that bovine DNase I both prevented biofilm formation and (to a certain extent) dissolved existing biofilm colonies. It was concluded that extracellular DNA is required for the initial establishment of *P. aeruginosa* biofilms, which is later strengthened by other substances such as exopolysaccharides and proteins (Whitchurch et al. 2002. Science, 295: 1487).

Purified recombinant human DNase1L2 was shown to suppress biofilm formation by *Pseudomonas aeruginosa* and *Staphylococcus aureus* (Eckhart et al. 2007. British Journal of Dermatology, 156(6): 1342-1345; Tetz et al. 2009. Antimicrobial Agents & Chemotherapy, 53(3): 1204-1209).

It has been shown that type IV pilli of *Pseudomonas aeruginosa* bind DNA, and that this function is conserved throughout the type IV pilli in bacteria (van Schaik et al. 2005. Journal of Bacteriology, 187(4) 1455-1464). Both DNA and type IV pilli are involved in the attachment to a surface, the initial stage of biofilm formation.

Furthermore, it has recently been described that in single species biofilms of *Bacillus cereus* or the marine photosynthetic bacterium *Rhodovulum* sp. not only DNA but also RNA is present in the extracellular matrix (Vilain et al. 2009. Applied and Environmental Microbiology, 75(9): 2861-2868; Ando et al. 2006. Journal of Biochemistry, 139: 805-811).

In view of the above, it is clear that DNA and RNA are structural components of biofilm and that alternative, more effective nuclease enzymes, other than bovine DNase 1 would be beneficial in terms of biofilm disruption and prevention in a range of applications, including medical and non-medical anti-biofouling applications.

In particular, the removal of biofilms in medical contexts currently poses significant problems since the bacteria present in the biofilm are highly resistant to many antimicrobial compounds. Furthermore, prior art methods for biofilm disruption involve compositions active against mainly only gram negative proteobacteria, and show very specific activity against a limited number of strains. This significantly limits their utility. Thus, there remains a need for new biofilm disruption and prevention methods and strategies involving compositions with improved properties.

SUMMARY OF THE INVENTION

Whilst the prior art recognises DNA and RNA as structural components of biofilm, the present inventors have discovered that surprisingly, microbes actively employ their own nucleases, in particular deoxyribonucleases, in order to influence the biofilm in which they naturally grow. Thus, prior to the current discovery, it was not realised or appreciated that microbes have what appears to be a much more dynamic relationship with the biofilm. Whilst DNA molecules are structural components of biofilms, they are, surprisingly, far from being merely "passive" ingredients as previously considered. The current inventors have discovered that microbes secrete nucleases, in particular deoxyribonucleases which can degrade DNA within the biofilm and that microbes have evolved the ability to do this in a controlled and precise manner so as to carefully manipulate the properties of the biofilm and thus the environmental milieu in which they naturally grow.

As such, based on this surprising discovery, it is apparent that microbial deoxyribonucleases will possess superior biofilm disruption and prevention activities not least because they have evolved, inter alia, the ability to precisely degrade biofilm-specific extracellular DNA.

Thus, the invention provides a pharmaceutical composition or an anti-biofouling composition for disrupting a biofilm or preventing biofilm formation comprising an isolated microbial deoxyribonuclease polypeptide and an excipient.

The microbial nuclease component of the composition can be a bacterial deoxyribonuclease.

The microbial nuclease component of the composition can be a gram positive bacterial deoxyribonuclease.

The microbial nuclease component of the composition can be a class *Bacillus* bacterial deoxyribonuclease.

The microbial nuclease component of the composition can be a *Bacillus licheniformis* bacterial deoxyribonuclease.

The microbial nuclease component of the composition can be a *Bacillus licheniformis* strain EI-34-6 bacterial deoxyribonuclease.

The microbial nuclease component of the composition can be a bacterial nucB deoxyribonuclease.

The microbial nuclease component of the composition can be a *Bacillus licheniformis* strain EI-34-6 nucB deoxyribonuclease defined by SEQ ID NO. 6 or a deoxyribonuclease which is at least 95%, 90%, 85%, 80%, 75% or 70% identical thereto.

The pharmaceutical and anti-biofouling compositions of the invention can comprise one or more of the microbial deoxyribonucleases described herein in any combination.

In any of the pharmaceutical or anti-biofouling compositions described herein the microbial deoxyribonuclease(s) can be extracellular deoxyribonucleases.

In any of the pharmaceutical or anti-biofouling compositions described herein the composition can be formulated as a liquid, lotion, cream, spray, gel, ointment, washing powder, or cleaning agent such as a cleaning solution, cleaning liquid, cleaning lotion, cleaning cream, cleaning spray, cleaning gel and the like.

In any of the pharmaceutical or anti-biofouling compositions described herein the composition can be formulated as a dental paste, a liquid dentifrice, a mouthwash, a troche or a gingival massage ointment.

Any of the pharmaceutical compositions described herein can be formulated for use in the treatment of a wide range of medical indications.

Any of the anti-biofouling compositions described herein can be formulated for use in a wide variety of cleaning applications. Thus, the anti-biofouling compositions of the invention can be formulated, for example, as a washing powder composition, as a surface cleaning composition, as a liquid, lotion cream, spray, gel, ointment or cleaning solution.

Any of the pharmaceutical or anti-biofouling compositions described herein may additionally comprise one or more of an antibacterial compound, an antiparasitic compound, an antiviral compound and an antifungal compound.

The antiparasitic compound can be one or more of a benzazole, such as albendazole, mebendazole and tiabendazole; an azole, such as metronidazole and tinidazole; a macrocycle, such as amphotericin B, rifampin and ivermectin; pyrantel pamoate; diethylcarbamazine; niclosamide; praziquantel; melarsopro; and eflornithine.

The antiviral compound can be one or more of a nucleoside analog reverse transcriptase inhibitor, such as acyclovir, didanosine, stavudine, zidovudine, lamivudine, abacavir, emtricitabine and entecavir; an uncoating inhibitor such as amantadine, rimantadine and pleconaril; a protease inhibitor such as saquinavir, ritonavir, indinavir, nelfinavir and amprenavir; zanamivir; oseltamivir; and rifampin.

The antibacterial compound can be one or more of an aminoglycoside such as gentamicin, kanamycin and streptomycin; a beta-lactam such as penicillin, ampicillin and imipenem; a cephalosporin such as ceftazidime, a quinolone such as ciprofloxacin; a macrolide such as azithromycin, clarithromycin, dirithromycin, erythromycin, roxithromycin and telithromycin; an oxazolidinone such as linezolid; an ansamycin such as rifamycin; a sulphonamide; a tetracycline such as doxycycline; a glycopeptide such as vancomycin; sulfisoxazole, trimethoprim, novobiocin, daptomycin and linezolid.

The antifungal compound can be one or more of an azole, such as miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole and abafungin; a macrocycle, such as natamycin, rimocidin, filipin, nystatin, amphotericin B, candicin, hamycin; an allyl amine such as terbinafine, naftifine and butenafine; an echinocandin such as andidulafungin, caspofungin and micafungin; or others such as polygodial, ciclopirox, tolnaftate, benzoic acid, undecylenic acid, flucytosine and griseofulvin.

Where the composition is a pharmaceutical composition, said composition can be for administration to an animal patient. The animal patient can be a mammalian patient. The mammalian patient can be a human.

Where the composition is an anti-biofouling composition, the antibacterial compound can additionally be one or more of a parahydroxy benzoic acid ester (parabens), such as methyl-paraben, ethyl-paraben, propyl-paraben, butyl-paraben and benzyl-paraben.

The invention also provides any of the above-mentioned isolated microbial nuclease polypeptide(s) for use as a pharmaceutical, together with a physiologically acceptable carrier, excipient or diluent.

The invention also provides any of the above-mentioned isolated microbial nuclease polypeptide(s) for use in the manufacture of a medicament.

Any of the above-mentioned isolated microbial deoxyribonuclease polypeptide(s), are provided when used as a pharmaceutical or when used in the manufacture of a medicament, can be used in the treatment of conditions including dental plaque; dental caries; periodontitis; native valve endocarditis; chronic bacterial prostatitis; otitis media; infections associated with medical devices such as artificial heart valves, artificial pacemakers, contact lenses, prosthetic joints, sutures, catheters, and arteriovenous shunts; infections associated with wounds, lacerations, sores and mucosal lesions such as ulcers; infections of the mouth, oropharynx, nasopharynx and laryngeal pharynx; infections of the outer ear; infections of the eye; infections of the stomach, small and large intestines; infections of the urethra and vagina; infections of the skin; intra-nasal infections, such as infections of the sinus.

The invention also provides a method of disrupting a biofilm on a patient comprising contacting a biofilm on a patient with any of the pharmaceutical compositions described herein.

The invention also provides a method of preventing the formation of a biofilm on a patient comprising contacting a surface of a patient susceptible to biofilm formation with any of the pharmaceutical compositions described herein.

The patient can be an animal patient. The patient can be a mammalian patient. The patient can be a human.

The invention also provides a method of preventing the formation of a biofilm on a medical device comprising contacting a surface of a medical device with any of the pharmaceutical or anti-biofouling compositions described herein. Optionally, the microbial deoxyribonuclease(s) of said compositions can be attached to said surface. The medical device may be any medical device as described herein.

As such, the invention also provides an indwelling medical device as described herein characterised in that at least a portion of a patient-contactable surface of said device is coated with any of the pharmaceutical or anti-biofouling compositions described herein. Such a device can be, for example, a catheter or a canula. In such devices, the microbial deoxyribonuclease(s) of the composition can be attached to said at least a portion of a patient-contactable surface.

Also provided is a method of disrupting a biofilm on a surface comprising contacting a biofilm on a surface with any of the anti-biofouling compositions described herein.

Also provided is a method of preventing the formation of a biofilm on a surface comprising contacting a surface with any of the anti-biofouling compositions described herein.

In any of these methods the microbial deoxyribonuclease(s) of the anti-biofouling composition can be attached to said surface.

In any of these methods the biofilm can comprise gram positive bacteria.

The invention also provides for the use of any of the isolated microbial deoxyribonuclease polypeptide(s) described herein in the manufacture of an anti-biofouling composition for disrupting a biofilm or preventing biofilm formation. Such a composition can be formulated for example as a powder, a liquid, a gel or a paste.

For example, the composition can be formulated as a liquid, lotion, cream, spray, gel, ointment, washing powder, or cleaning agent such as a cleaning solution, cleaning liquid, cleaning lotion, cleaning cream, cleaning spray, cleaning gel and the like.

Such a composition can be for application to a surface, wherein said surface is at least a portion of a surface of a kitchen, such as a floor, bench, wall or sink unit; or a kitchen appliance, such as an oven, refrigerator or freezer. In such applications, typically the composition will be a liquid spray or a formulation for topical application, such as a gel, paste, cream, spray or cleaning solution.

Such a composition can be for application to at least a portion of a surface of a component of, for example, a water distribution apparatus; a water storage apparatus; a heat transfer apparatus; a water treatment apparatus; a cooling apparatus; a hull of a nautical vessel such as a ship, a boat, a yacht or a submarine. In these applications, optionally the microbial nuclease polypeptide(s) of such a composition can be attached to a surface.

The invention also provides an expression vector comprising a polynucleotide encoding any of the above-described microbial deoxyribonuclease polypeptide(s).

DESCRIPTION OF THE FIGURES

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 shows NucB protein sequence (SEQ ID NO:5) from the sequenced genome of *B. licheniformis* DSM13 was compared to NucB protein sequence (SEQ ID NO:3) from the environmental isolate *B. licheniformis* EI-43-6.

FIG. 6 shows the DNA sequence of *Bacillus licheniformis* nucB from strain EI-34-6 (SEQ ID No: 1).

FIG. 7 shows the DNA sequence of *Bacillus licheniformis* nucB from strain DSM13 (SEQ ID No: 2).

FIG. 8 shows the derived sequence of *Bacillus licheniformis* nucB protein precursor from strain EI-34-6. The sequence underlined is the predicted signal peptide sequence. (SEQ ID No: 3).

FIG. 9 shows the derived sequence of *Bacillus licheniformis* nucB protein precursor from strain EI-34-6 without the predicted signal peptide sequence. (SEQ ID No: 4).

FIG. 10 shows the derived sequence of *Bacillus licheniformis* nucB protein precursor from strain DSM13. The sequence underlined is the predicted signal peptide sequence. (SEQ ID No: 5).

DETAILED DESCRIPTION OF THE INVENTION

Figure 1:
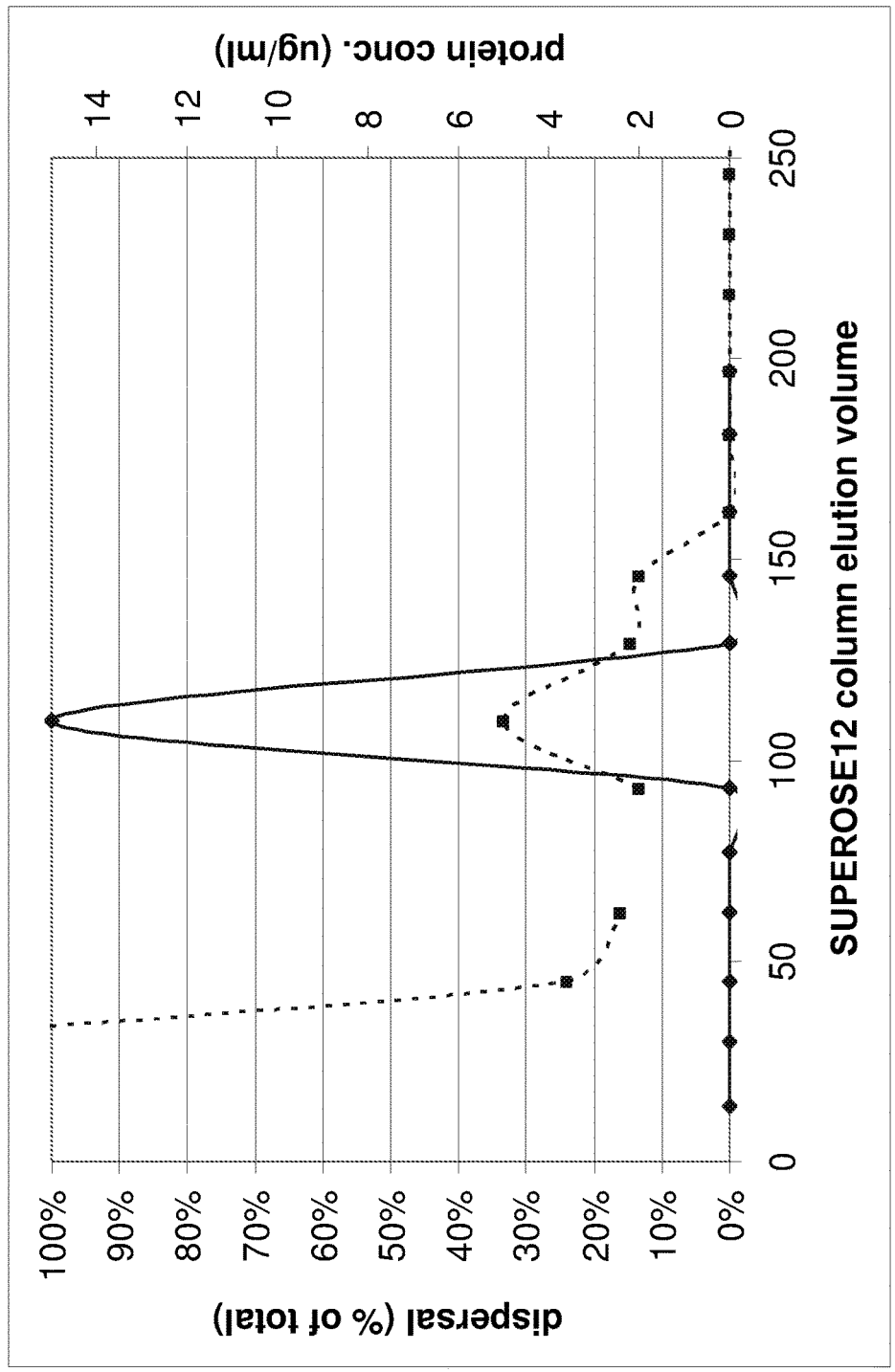
FIG. 1 shows a plot of concentration of SUPEROSE 12 fractions of TCA-concentrated *B. licheniformis* strain EI-34-6 AMS supernatant (dashed line) against the percentage biofilm dispersal activity (solid line).

As noted above, biofilms are associated with the pathogenesis of a significant number of infections in humans and other organisms and cause significant problems in industry in terms of biofouling. Consequently, new strategies are required to inhibit biofilm formation and to disperse pre-existing biofilm. In medical and industrial applications, disruption of pre-existing biofilm can lead per se to the eradication of the microorganisms due to disruption of the microbial growth-supporting environment. Disruption can also render the microbe inhabitants of the biofilm more susceptible to anti-microbial compounds.

The present invention is based on the discovery that, surprisingly, microbes can actively modify the biofilm in which they grow by the secretion of nuclease enzymes. As such, the extracellular nucleic acid, in particular DNA, components of biofilm appear to be structural components of biofilm which can specifically be targeted for degradation by inhabitant microbes via nucleases particularly deoxyribonucleases. The unique and harsh composition of the biofilm, comprising a viscous agglomeration of polymeric matrix, macromolecules and the like, indicates a requirement for nucleases with higher specific activity for the extracellular nucleic acid component of biofilm. As such, microbial deoxyribonucleases provide for more effective biofilm-specific extracellular nucleic acid degrading agents.

The invention therefore provides compositions comprising microbial deoxyribonucleases for disrupting biofilm or preventing biofilm formation in both medical applications and in non-medical (anti-biofouling or cleaning) applications as described in more detail below.

As described herein, microbial deoxyribonuclease polypeptides were identified by biofilm disrupting activity-directed fractionation of *B. licheniformis* growth media followed by peptide mass spectrometric fingerprinting and subsequent cloning of genes encoding proteins specific to the active fraction. Microbial deoxyribonuclease polypeptides can be isolated and formulated for pharmaceutical and anti-biofouling compositions for disrupting biofilm and preventing biofilm formation as described herein.

An "isolated" microbial deoxyribonuclease polypeptide as used herein refers to a microbial deoxyribonuclease polypeptide that has been separated from other proteins, lipids, nucleic acids or other macromolecules with which it naturally occurs/associates or the polypeptide may be synthetically synthesised and purified by standard techniques. The polypeptide is also separated from substances, for example, antibodies or gel matrix, for example, polyacrylamide, which can be used to purify it. Preferably, the polypeptide constitutes by weight at least 60% or more, 70% or more, 80% or more, 90% or more, or 95% or more of a purified microbial nuclease preparation for use in the compositions of the invention.

The terms nuclease or deoxyribonuclease as used herein can refer to a full-length polypeptide(s). The term can also refer to a biologically-active fragment of such a polypeptide(s), such as a truncated polypeptide, or a genetically modified form or either a full-length or truncated fragment, provided that the biological activity of the molecule is retained.

The pharmaceutical formulations comprising the microbial deoxyribonuclease compositions described herein can be administered, inter alia intravenously, intraperitoneally, intramuscularly, subcutaneously, intracavity, orally and by inhalation.

The pharmaceutical formulations comprising the microbial deoxyribonuclease compositions described herein can be formulated for topical administration (e.g., as a lotion, cream, spray, gel, or ointment). Such topical formulations are useful in treating or inhibiting microbial or fungal presence or infections on bio-devices, contaminated surfaces, the eye, skin, and mucous membranes such as mouth, vagina and the like.

Examples of formulations include topical lotions, creams, soaps, wipes, and the like. They may be formulated into liposomes, to reduce toxicity or increase bioavailability. Other methods for delivery include oral methods that entail encapsulation of the polypeptide or peptide in microspheres or proteinoids, aerosol delivery (e.g., to the lungs), or transdermal delivery (e.g., by iontophoresis or transdermal electroporation). Other routine methods of administration will be known to those skilled in the art.

Any suitable pharmaceutically acceptable excipient can be used in the manufacture of pharmaceutical compositions comprising the microbial deoxyribonucleases described herein. Such excipients, carriers, vehicles etc are well known to those of skill in the art and are described in text books such as Remington's Pharmaceutical Sciences, Mack Publishing Co., Easton, Pa., 1985.

Pharmaceutical formulations, containing any of the microbial deoxyribonuclease compositions described herein, suitable for oral administration may be provided in convenient unit forms including capsules, tablets, gels, pastes, ointments etc.

Oral compositions containing any of the microbial deoxyribonuclease pharmaceutical compositions described herein may be prepared and used in various forms applicable to the mouth such as toothpastes, liquid dentifrices, mouthwashes, troches, dental pastes, gingival massage ointments, and other suitable embodiments. Such an oral composition may further include additional well known ingredients depending on the type and form of the particular oral composition.

The oral composition may be substantially liquid in character, such as a mouthwash or rinse. In such a preparation the vehicle is typically a water-alcohol mixture, possibly including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically isopropanol, preferably ethanol.

The pH of such liquid and other microbial deoxyribonuclease pharmaceutical compositions described herein is generally in the range of from about 5 to about 9 and typically from about 5 to about 7. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Any of the microbial deoxyribonuclease pharmaceutical compositions described herein may be substantially solid or pasty in character, such as toothpowder, a dental tablet, a toothpaste, a dental cream/ointment and a gel dentifrice.

In a toothpaste, the liquid vehicle may comprise water and a humectant, typically the humectant is present in an amount from about 10% to about 80% by weight. Suitable humectants include glycerine, sorbitol, propylene glycol, and polypropylene glycol. Advantageous are liquid mixtures of water, glycerine and sorbitol. In clear gels, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. Suitable thickeners include synthetic hectorite, Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose, sodium carboxymethyl cellulose, and colloidal silica.

Solubilising agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

Anionic surfactants can be used, such as higher alkyl sulphates such as sodium lauryl sulphate, higher alkylsulpho-acetates, higher fatty acid esters of 1,2-dihydroxy propane sulphonate, alkyl aryl sulphonates such as sodium dodecyl benzene sulphonate, and water-soluble salts of higher fatty acid monoglyceride monosulphates. Other specific surfactants include N-lauroyl sarcosine; the sodium, potassium, and ethanolamine salts of N-lauroyl, N-myristoyl, or N-palmitoyl sarcosine. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Pharmaceutically acceptable excipients which are suitable for use in tablet formulations include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

For hard gelatin capsule formulations, the active ingredient can be mixed with an inert solid diluent, for example, calcium carbonate, calcium phosphate or kaolin. For soft gelatin capsule formulations the active ingredient can be mixed with water or an oil medium, for example peanut oil, liquid paraffin or olive oil.

Excipients suitable for the manufacture of aqueous suspensions include suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

Aqueous suspensions may also contain one or more preservatives, for example benzoates, such as ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents and flavouring agents may be added. These compositions may be preserved by the addition of an antioxidant such as ascorbic acid.

Any of the microbial deoxyribonuclease pharmaceutical compositions described herein may also be formulated for parenteral administration, such as by injection, for example bolus injection or continuous infusion, and may be provided in unit dose form in ampules, pre-filled syringes, small volume infusion or in multi-dose containers, e.g. with an added preservative.

Preparations for parenteral administration of pharmaceutical formulations comprising the microbial deoxyribonuclease compositions described herein include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

For topical administration to the epidermis, any of the microbial deoxyribonuclease pharmaceutical compositions may be formulated as an ointment, cream, or lotion. Ointments and creams, may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges, e.g. in a flavoured base, usually sucrose and acacia or tragacanth; pastilles comprising the active ingredient in an inert base such as gelatin and glycerin or sucrose and acacia; and mouth washes comprising the active ingredient in a suitable liquid carrier.

For topical administration to the eye, any of the microbial deoxyribonuclease pharmaceutical compositions can be made up in solution or suspension in a suitable sterile aqueous or non-aqueous vehicle. Additives such as buffers (e.g. sodium metabisulphite or disodium edeate) and thickening agents such as hypromellose can also be included.

For intra-nasal administration, any of the microbial deoxyribonuclease pharmaceutical compositions can be provided in a liquid spray or dispersible powder or in the form of drops. Drops may be formulated with an aqueous or non-aqueous base also comprising one or more dispersing agents, solubilising agents, or suspending agents.

For administration by inhalation, any of the microbial deoxyribonuclease pharmaceutical compositions can be delivered by insufflator, e.g. a nebulizer or a pressurized pack or other convenient means of delivering an aerosol spray. Pressurised packs may comprise a suitable propellant.

In the case of a pressurised aerosol the dosage unit may be determined by providing a value to deliver a metered amount.

Any of the microbial deoxyribonuclease pharmaceutical compositions described herein can take the form of a dry powder composition, for example a powder mix of the active component and a suitable powder base such as lactose or starch. The powder composition may be presented in unit dosage form in, for example, capsules, cartridges or blister packs of gelatins, from which the powder can be administered with the aid of an inhalator or insufflator.

Wound dressings such as sponges, gauzes, bandages, plasters etc can be impregnated with the microbial deoxyribonuclease pharmaceutical compositions to prevent or inhibit bacterial or fungal attachment and reduce the risk of wound infections.

Catheter shields as well as other materials used to cover catheter insertion sites can be coated or impregnated with microbial deoxyribonuclease pharmaceutical compositions to inhibit bacterial or fungal biofilm attachment thereto.

Additional medical devices which can be coated with the microbial deoxyribonuclease pharmaceutical compositions include central venous catheters, intravascular catheters, urinary catheters, Hickman catheters, peritoneal dialysis catheters, endrotracheal catheters, mechanical heart valves, cardiac pacemakers, arteriovenous shunts, schleral buckles, prosthetic joints, tympanostomy tubes, tracheostomy tubes, voice prosthetics, penile prosthetics, artificial urinary sphincters, synthetic pubovaginal slings, surgical sutures, bone anchors, bone screws, intraocular lenses, contact lenses, intrauterine devices, aortofemoral grafts and vascular grafts. Exemplary solutions for impregnating gauzes or sponges, catheter shields and adhesive drapes or coating catheter shields and other medical devices include, but are not limited to, phosphate buffered saline (pH approximately 7.5) and bicarbonate buffer (pH approximately 9.0).

The microbial deoxyribonuclease pharmaceutical compositions described herein can be incorporated into a liquid disinfecting solution. Such solutions may further comprise antimicrobials or antifungals such as alcohol, providone-iodine solution and antibiotics as well as preservatives. These solutions can be used, e.g., as disinfectants of the skin or surrounding area prior to insertion or implantation of a device such as a catheter, as catheter lock and/or flush solutions, and as antiseptic rinses for any medical device including, but not limited to catheter components such as needles, Luer-Lok connectors, needleless connectors and hubs as well as other implantable devices. These solutions can also be used to coat or disinfect surgical instruments.

The amount of microbial deoxyribonuclease required for use in treatment will of course vary not only with the particular polypeptide but also with the route and form of administration, the nature and severity of the condition being treated, and the age and condition of the organism.

Furthermore, the extent of the disruption of the biofilm may be modulated, as required, by the dose of the microbial deoxyribonuclease component of the composition. For instance, a smaller dose of the microbial deoxyribonuclease component may lead to permeabilization of the biofilm, rather than more extensive structural disruption which might be achieved at higher doses. Such permeabilization may lead to portals in the biofilm through which entrapped microbes can exit and/or through which additional antimicrobial components of the composition can penetrate.

Thus, appropriate concentrations of the active microbial deoxyribonuclease to be incorporated into pharmaceutical compositions can be routinely determined by those skilled in the art in accordance with standard practices.

In view of the above, an effective dosage of the microbial deoxyribonuclease component is a dosage that is assessed to lead to a detectable disruption of biofilm, or reduction in biofilm formation, as compared to in the absence of the microbial deoxyribonuclease component. For example, doses can include between about 1 milligram kilogram$^{-1}$ to 1 gram kilogram$^{-1}$ by body weight of the animal being treated, between about 0.01 milligram kilogram$^{-1}$ to 100 milligram kilogram$^{-1}$ by body weight of the animal being treated, between about 0.01 microgram kilogram$^{-1}$ and about 10 milligram kilogram$^{-1}$ by body weight of the animal being treated, between about 0.1 microgram and about 10 microgram kilogram$^{-1}$ body weight of an animal, between about 1 microgram and about 10 milligram kilogram$^{-1}$ body weight of an animal, between about 5 microgram and about 10 milligram kilogram$^{-1}$ body weight of an animal, between about 10 microgram and about 10 milligram kilogram$^{-1}$ body weight of an animal, between about 0.1 milligram and about 5 milligram kilogram$^{-1}$ body weight of an animal.

Pharmaceutical formulations comprising the microbial deoxyribonuclease compositions described herein can also include an antimicrobial agent such as detergents and antibiotics. Suitable antibiotics include aminoglycosides (e.g., gentamicin, kanamycin and streptomycin), beta-lactams (e.g., penicillin, ampicillin, imipenem and cephalosporins such as Ceftazidime), quinolones (e.g., ciprofloxacin), macrolides such as azithromycin, clarithromycin, dirithromycin, erythromycin, roxithromycin and telithromycin, oxazolidinones such as linezolid, ansamycins such as rifamycin, sulfonamides, tetracyclines such as Doxycycline. Additional antibiotics include glycopeptides such as vancomycin, sulfisoxazole, trimethoprim, novobiocin, daptomycin and linezolid.

Generally, the antimicrobial is administered in a microbicidal amount. However, the antimicrobial can also be administered in microbistatic amount. Regardless, the pharmaceutical formulations comprising the microbial deoxyribonuclease compositions described herein provide for an elevated antimicrobial activity by virtue of the disruption of the biofilm in which the particular microbe exists, together with additional antimicrobial compounds if required.

Biofilms may also harbour parasites and viruses. Consequently, antiparasitic and/or antiviral compounds can also be included in the pharmaceutical compositions described herein, optionally together with an antibacterial compound, such as those specified above.

Antiparasitic compounds which can be included in the pharmaceutical compositions of the invention include the benzazoles (albendazole, mebendazole, tiabendazole, etc.), the azoles (metronidazole, tinidazole, etc.), macrocycles (amphotericin B, rifampin, ivermectin etc.) and others such as pyrantel pamoate, diethylcarbamazine, niclosamide, praziquantel, melarsoprol and eflornithine.

Antiviral compounds which can be included in the pharmaceutical compositions of the invention include the nucleoside analog reverse transcriptase inhibitors (acyclovir, didanosine, stavudine, zidovudine, lamivudine, abacavir, emtricitabine, entecavir etc.), uncoating inhibitors (amantadine, rimantadine, pleconaril etc.), protease inhibitors (saquinavir, ritonavir, indinavir, nelfinavir, amprenavir, etc.) and others such as zanamivir, oseltamivir, rifampin.

Antiviral compounds which can be included in the pharmaceutical compositions of the invention include an azole, such as miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole and abafungin; a macrocycle, such as natamycin, rimocidin, filipin, nystatin, amphotericin B, candicin, hamycin; an allyl amine such as terbinafine, naftifine and butenafine; an echinocandin such as andidulafungin, caspofungin and micafungin; or others such as polygodial, ciclopirox, tolnaftate, benzoic acid, undecylenic acid, flucytosine and griseofulvin.

Whilst treatment of human patients is clearly envisaged, the microbial deoxyribonuclease pharmaceutical compositions of the invention equally find utility in the treatment of non-human mammals and other animals. Thus, the pharmaceutical compositions of the invention find utility in veterinary medicine and treatment.

Although not limiting on the invention, various microbes that can be affected by the microbial deoxyribonuclease pharmaceutical compositions described herein are mentioned below.

Bacteria that can be affected by the microbial deoxyribonuclease pharmaceutical compositions described herein include both gram-negative and gram-positive bacteria. For example, bacteria that can be affected include *Staphylococcus aureus*, *Streptococcus pyogenes* (group A), *Streptococcus* sp. (*viridans* group), *Streptococcus agalactiae* (group B), *S. bovis*, *Streptococcus* (anaerobic species), *Streptococcus pneumoniae*, and *Enterococcus* sp.; gram-negative cocci such as, for example, *Neisseria gonorrhoeae*, *Neisseria meningitidis*, and *Branhamella catarrhalis*; gram-positive bacilli such as *Bacillus anthracis*, *Bacillus subtilis*, *Propionibacterium acnes*, *Corynebacterium diphtherias* and *Corynebacterium* species which are diptheroids (aerobic and anerobic), *Listeria monocytogenes*, *Clostridium tetani*, *Clostridium difficile*, *Escherichia coli*, *Enterobacter species*, *Proteus mirablis* and other sp., *Pseudomonas aeruginosa*, *Klebsiella pneumoniae*, *Salmonella*, *Shigella*, *Serratia*, and *Campylobacter jejuni*. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections.

Fungal microbial organisms which may also be affected by pharmaceutical formulations comprising the microbial deoxyribonuclease compositions described herein include dermatophytes (e.g., *Microsporum canis* and other *Microsporum* sp.; and *Trichophyton* sp. such as *T. rubrum*, and *T. mentagrophytes*), yeasts (e.g., *Candida albicans*, *C. tropicalis*, or other *Candida* species), *Saccharomyces cerevisiae*, *Torulopsis glabrata*, *Epidermophyton floccosum*, *Malassezia furfur* (*Pityropsporon orbiculare*, or *P. ovale*), *Cryptococcus neoformans*, *Aspergillus fumigatus*, *Aspergillus nidulans*, and other *Aspergillus* sp., Zygomycetes (e.g., *Rhizopus*, *Mucor*), *Paracoccidioides brasiliensis*, *Blastomyces dermatitides*, *Histoplasma capsulatum*, *Coccidioides immitis*, and *Sporothrix schenckii*.

Microbes which can colonise the mouth & oropharynx and which can be treated with the pharmaceutical compositions comprising the microbial deoxyribonucleases described herein include the following. *Actinomyces*, *Bacteroides*, *Candida*, *Corynebacterium*, *Eikenella corrodens*, Enterobacteriaceae, *Fusobacterium*, *Haemophilus* sp. including *Haemophilus influenzae*, *Kingella*, *Lactobacillus*, *Moraxella* sp. including *Moraxella catarrhalis*, *Mycoplasma*, *Neisseria*, *Peptostreptococcus*, Staph. *aureus*, Staph. *epidermidis*, Strep. *viridams*, Strep. *pyogenes*, Strep *pneumoniae*, *Treponema* and *Pseudomonas aeruginosa*.

Microbes which can colonise the nasopharynx and which can be treated with the pharmaceutical compositions comprising the microbial deoxyribonucleases described herein include the following. *Haemophilus*, *Neisseria*, Staph. *aureus*, Staph. *epidermidis*, Strep. *viridans* and Strep. *pneumoniae*.

Microbes which can colonise the outer ear and which can be treated with the pharmaceutical compositions comprising the microbial deoxyribonucleases described herein include the following. Enterobacteriaceae, *Pseudomonas*, Staph. *epidermidis* and Strep. *pneumoniae*.

Microbes which can colonise the eye and which can be treated with the pharmaceutical compositions comprising the microbial deoxyribonucleases described herein include the following. *Haemophilus* and Staph. *epidermidis*.

Microbes which can colonise the stomach and which can be treated with the pharmaceutical compositions comprising the microbial deoxyribonucleases described herein include the following. *Helicobacter pylori*, *Lactobacillus* and *Streptococcus*.

Microbes which can colonise the small intestine and which can be treated with the pharmaceutical compositions comprising the microbial deoxyribonucleases described herein include the following. *Bacteroides*, *Candida*, *Clostridium*, Enterobacteriaceae, *Enterococcus*, *Fusobacterium*, *Lactobacillus*, *Peptostreptococcus*, *Staphylococcus*, and *Streptococcus*.

Microbes which can colonise the large intestine and which can be treated with the pharmaceutical compositions comprising the microbial deoxyribonucleases described herein include the following. *Bacteroides*, *Candida*, *Clostridium*, *Corynebacterium*, Enterobacteriaceae, *Enterococcus*, *Fusobacterium*, *Lactobacillus*, *Mycobacterium*, *Peptostreptococcus*, *Pseudomonas*, *Staphylococcus* and *Streptococcus*.

Microbes which can colonise the anterior urethra and which can be treated with the pharmaceutical compositions comprising the microbial deoxyribonucleases described herein include the following. *Candida*, *Corynebacterium*, Enterobacteriaceae, *Enterococcus*, Gardneralla *vaginalis*, *Lactobacillus*, *Mycoplasma*, Staph. *epidermidis*, *Streptococcus* and *Ureaplasma*.

Microbes which can colonise the vagina and which can be treated with the pharmaceutical compositions comprising the microbial deoxyribonucleases described herein include the following. *Actinomyces*, *Bacteroides*, *Candida*, *Clostridium*, Enterobacteriaceae, *Enterococcus*, *Fusobacterium*, *Gardnerella vaginalis*, *Lactobacillus*, *Mobiluncus*, *Mycoplasma*, *Staphylococcus*, *Streptococcus*, *Torulopsis* and *Ureaplasma*.

Microbes which can colonise the skin and which can be treated with the pharmaceutical compositions comprising the microbial deoxyribonucleases described herein include the following. *Candida*, *Clostridium*, *Corynebacterium*, *Proprionibacterium*, Staph. *aureus*, Staph. *epidermidis* and Strep. *pyogenes*.

Specific diseases and infections are associated with biofilm (Costerton et al. Science 1999 284:1318-1322; Donlan, R. M. 2001 Emerging Infect. Dis. 7:277-281, Donlan, R. M., and J. W. Costerton. 2002. Clin. Microbiol. Rev. 15:167-193.). For instance, diseases include dental caries, periodontitis, native valve endocarditis, chronic bacterial prostatitis and otitis media. Furthermore, biofilms have been associated with the infection of various indwelling medical devices such as artificial heart valves, artificial pacemakers, contact lenses and prosthetic joints. Biofilm-associated infections including those associated with catheters, especially intravascular catheters, are common in hospitalised patients and are associated with high morbidity and mortality. Biofilms have been proven to play an important role in infections at sutures, exit sites, arteriovenous shunts, urinary tract-, central venous- and Hickman catheters and orthopaedic devices, and other similar devices. Fungi (e.g. *Candida albicans*) also form disease-associated biofilms. Microbes associated with infections of the lung and infections arising from wounds, lacerations, sores, ulcers and other such lesions may also be treated with the pharmaceutical compositions comprising the microbial deoxyribonucleases described herein.

Any one of the microbial deoxyribonucleases described herein, or combinations thereof, can be coated onto the surface of at least a portion of a medical device intended for contact with a patient, so as to prevent biofilm formation on surfaces of such devices susceptible to biofilm formation. In addition, the microbial deoxyribonucleases described herein, or combinations thereof, can be immobilised onto such surfaces.

Strategies for immobilisation of proteins and peptides onto derivatized surfaces are well known in the art and have been employed in many applications, for example in the manufacture of protein microarrays (see for example; Yeo et al. Combinatorial Chemistry and High Throughput Screening. 2004. 7(3): 213-221; Camarero J. Biopolymers. 2008. 90(3): 450-458; Köhn, M. Journal of Peptide Science 2009. 5(6):393-397). Such strategies can be employed in an analogous manner in the attachment of the microbial deoxyribonucleases of the invention to appropriate surfaces.

WO 2007/007052, for example, describes the use of a polysilane polymer for attachment of, inter alia, biologically active molecules to surfaces without loss of biological activity. The polymer forms a substantially three-dimensional porous network upon which and within which biological molecules can be absorbed. Devices, such as medical devices, which are functionalised with biomacromolecules using the disclosed technology are described.

Immobilisation onto surfaces susceptible to biofilm formation will typically relate to indwelling medical devices of the disposable variety, or devices intended for single use. Such devices will typically be catheters, canulas and the like.

Periodontal diseases, which can involve biofilms, range from simple gum inflammation to serious disease associated with the teeth. Periodontal disease includes gingivitis and periodontitis. Bacteria, such as *P. gingivalis*, cause inflammation of the gums, a condition known as gingivitis. In gingivitis, the gums become red, swollen and can bleed easily. When gingivitis remains untreated, it can advance to periodontitis where the gums detach from the teeth and form pockets which can become infected and which can subsequently lead to destruction of gums, underlying bone and connective tissue that support the teeth, ultimately leading to tooth loss if untreated.

Those skilled in the art of medicine can readily employ conventional criteria to identify appropriate subjects for treatment with the pharmaceutical formulations comprising the microbial deoxyribonucleases described herein. However, examples of other diseases that can be treated with the compositions described herein include essentially any infection associated with gram-positive or gram-negative bacteria or a fungus and known or suspected to involve biofilm-directed growth. Diseases and conditions which can be treated include fever, toxic shock, organ failure, adult respiratory distress syndrome and the like.

The present invention also finds utility in non-medical anti-biofouling/cleaning applications in the prevention of biofilm formation or disruption of established biofilm on natural and artificial surfaces of in, for example, industrial, commercial, agricultural and domestic settings.

Biofilms can lead to contamination of a wide variety of surfaces in such contexts, as described further below, such as water distribution networks, water storage equipment, water treatment equipment, heat transfer equipment, cooling towers and so forth.

The term "surface" is intended to include any surface in such non-medical contexts which can be contacted with water, in any of its solid, liquid or gaseous phases, particularly liquid water, water vapour, steam etc such that undesirable biofilm formation and build-up can arise as a result of colonisation by microorganisms. Typically, such formation and build-up can occur in damp, moist, misty and humid environments. Biofilm formation can also occur in submerged environments, in submerged environments which periodically can also be exposed to air (e.g. ship hulls at sea and in dry dock situations) and typically at water/air interfaces. As such, the invention finds utility in a wide range of non-medical anti-biofouling/cleaning applications.

Thus, the invention provides anti-biofouling compositions for disrupting a biofilm and for preventing biofilm formation, comprising the isolated microbial deoxyribonuclease polypeptides described herein and an excipient. An "anti-biofouling composition" as described herein is a composition intended for contact with any suitable "surface" as described above.

Typical water systems always contain a microbial population and are rarely sterile. There generally exists the potential for microbial multiplication, growth and bloom given the appropriate conditions (Industrial Antimicrobial Agents: Applications and Markets in Various Global Regions 2000-2005-2010' (Technical Insights) published by Frost and Sullivan). As such, submergible structures are particularly susceptible to biofilm formation and subsequent fouling. Typical field methods for the control of microbial growth are quick and are not comprehensive for total control.

Bacterial biofilms are a significant concern in industrial water systems, and are implicated in the fouling of water distribution networks, heat transfer equipment and the like. When dealing with cooling towers and spray ponds, algal biofilms are a common concern. Not only do these films foul distribution decks and tower fill, but the algae will provide the nutrients for the proliferation of bacteria and fungi. The formation of biofilms also leads to the trapping of inorganic salts and scale formation which further disrupts industrial equipment.

Another problem that is associated with biofilms is that of corrosion. The microorganisms within biofilms can influence corrosion by formation of localized differential cells, the production of mineral and organic acids, ammonia production, and sulphate reduction. The effective control of microorganisms with water treatment antimicrobial agents maintains the efficiency of the system in use and reduces potential health hazards.

Fouling of ship hulls, rigs and the like is yet another consequence of problematic biofilm. Such fouling starts with the build-up of a bacterial biofilm followed by algae, barnacles and other marine organisms. By preventing the initial formation of the bacterial biofilm, the establishment of other more problematic fouling organisms can be prevented.

Thus the anti-biofouling compositions for disrupting a biofilm and for preventing biofilm formation can be applied to at least a portion of a surface of a component of, for example, a water distribution apparatus; a water storage apparatus; a heat transfer apparatus; a water treatment apparatus; a cooling apparatus; a hull of a nautical vessel such as a ship, a boat, a yacht or a submarine. Many other such applications are envisaged.

Biofilm formation is also a significant problem in animal husbandry, for example in aquaculture. Biofilm development in aquaculture tanks can provide a source of contamination by opportunistic pathogens which can be detrimental to the heath of animals (particularly in early stage development, e.g. larval stage) in aquaculture facilities (Weitz et al. 2009. Systematic and Applied Microbiology, 32: 266-277). Additional anti-biofouling treatment methods will find utility in such situations.

Biofilms may also arise in domestic or other similar contexts. For example, undesirable biofilm formation may form the basis of contamination of refrigerators, domestic water storage and supply equipment, drains, toilets and so forth.

Thus the anti-biofouling compositions for disrupting a biofilm and for preventing biofilm formation can be applied to at least a portion of a surface of a kitchen, such as a floor, bench, wall or sink unit; or a kitchen appliance, such as an oven, refrigerator or freezer.

The anti-biofouling compositions of the invention can be formulated differently depending upon the particular application envisaged. Dry- and liquid-formulation technologies for enzyme-based compositions are well known in the art (see for example EP0304332, EP 0458845, U.S. Pat. No. 5,558,812, and U.S. Pat. No. 6,242,405). In particular, biological enzymes are commonly used in detergent compositions e.g. for textile and kitchen cleaning applications to increase the efficiency of cleaning. Enzyme-containing detergent formulations are well known in the art and the nuclease enzymes of the invention can be formulated in an analogous manner (see for example U.S. Pat. No. 4,106,991, EP0170360, EP0193829, EP1420878, WO 92/19709 and EP0511456 and references therein).

Biofilms have been postulated to act as sites of attachment and detachment for viruses and protozoan parasites, and, as such, may facilitate accumulation, shelter and dissemination of such pathogens in water distribution networks resulting in the spread of waterbourne diseases. Indeed, it has recently been shown that the protozoan parasites *Cryptosporidium parvum* (oocysts) and *Giardia lamblia* (cysts), as well as the viruses Poliovirus-1, PhiX174 and MS1, can attach to and persist in drinking water biofilm (Karim et al. Applied and environmental microbiology. 2008. 74(7): 2079-88). Furthermore, such parasites and viruses can transfer from the biofilm to the water phase, confirming that biofilms can act as a source of parasitic and viral contamination of water distribution networks and the like.

Thus, the invention provides anti-biofouling compositions for the treatment of parasites and viruses in systems exposed to water where biofilm development and growth is undesirable.

Anti-biofouling compositions of the invention may additionally include one or more of an antimicrobial compound, an antiparasitic compound, an antiviral compound and an antifungal compound. A plethora of such compounds are available and are limited merely insofar as they should be compatible with the biologically active microbial nucleases of the invention. Such compatibility can be readily assessed and established by routine methods.

With respect to antimicrobial compounds, nonoxidizing compounds are preferred. Such compounds act mostly by altering the cell wall permeability, thereby interfering with the delicate osmotic pressure involved in the bacterial respiration and the transfer of nutrients across the membrane. The rate of kill of these sophisticated antimicrobial agents is slower than that of oxidizers but provides longer-term protection against the organism present and those arising out of other sources of infection. Nonoxidizers have a broader spectrum of activity and have good compatibility with other water treatment chemicals.

Biologically compatible nonoxidizers include compounds of the phenol-based class. Parahydroxy Benzoic Acid Esters (Parabens) can be used, such as methyl-paraben, ethyl-paraben, propyl-paraben, butyl-paraben and benzyl-paraben and combinations thereof. Sodium and potassium salts of parabens allow for improved cold-water solubility, and thus compatibility with aqueous systems that cannot be heated.

Other antibacterial compounds that can be included in the anti-biofouling compositions of the invention include one or more of an aminoglycoside such as gentamicin, kanamycin and streptomycin; a beta-lactam such as penicillin, ampicillin and imipenem; a cephalosporin such as ceftazidime, a quinolone such as ciprofloxacin; a macrolide such as azithromycin, clarithromycin, dirithromycin, erythromycin, roxithromycin and telithromycin; an oxazolidinone such as linezolid; an ansamycin such as rifamycin; a sulphonamide; a tetracycline such as doxycycline; a glycopeptide such as vancomycin; sulfisoxazole, trimethoprim, novobiocin, daptomycin and linezolid.

Antiparasitic compounds which can be included in the anti-biofouling compositions of the invention include the benzazoles (albendazole, mebendazole, tiabendazole, etc.), the azoles (metronidazole, tinidazole, etc.), macrocycles (amphotericin B, rifampin, ivermectin etc.) and others such as pyrantel pamoate, diethylcarbamazine, niclosamide, praziquantel, melarsoprol and eflornithine.

Antiviral compounds which can be included in the anti-biofouling compositions of the invention include the nucleoside analog reverse transcriptase inhibitors (acyclovir, didanosine, stavudine, zidovudine, lamivudine, abacavir, emtricitabine, entecavir etc.), uncoating inhibitors (amantadine, rimantadine, pleconaril etc.), protease inhibitors (saquinavir, ritonavir, indinavir, nelfinavir, amprenavir, etc.) and others such as zanamivir, oseltamivir, rifampin.

Antifungal compounds which can be included in the anti-biofouling compositions of the invention includean azole, such as miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole and abafungin; a macrocycle, such as natamycin, rimocidin, filipin, nystatin, amphotericin B, candicin, hamycin; an allyl amine such as terbinafine, naftifine and butenafine; an echinocandin such as andidulafungin, caspofungin and micafungin; or others such as polygodial, ciclopirox, tolnaftate, benzoic acid, undecylenic acid, flucytosine and griseofulvin.

Although not limiting on the invention, various microbes that can be affected by the microbial nuclease anti-biofouling compositions described herein are mentioned below.

Bacteria which can be treated with the compositions of the invention include the following. *Achrombacter* sp., *Acinetobacter* sp. including *Aerobacter aerogeus; Alcali-* genes sp.; *Bacillus* sp. including *Bacillus cerius, Bacillus subtilus; Beggiatoa* sp.; *Brevibacterium* sp.; *Burkholderia cepacia, Citrobacter* sp.; *Clostridium* sp.; *Corynebacterium* sp.; *Crenothrix* sp.; *Desulfobacter* sp.; *Desulfovibrio* sp.; *Enterobacter* sp. including *Enterobacter aerogeus; Escherichia* sp. including *Escherichia coli.; Flavobacterium* sp.; *Gallionella* sp.; *Klebsiella* sp.; *Leptothrix* sp.; *Pseudomonas* sp. including *Pseudomonas aeruginosa, Pseudomonas alcaligenes, Pseudomonas cepacia, Pseudomonas fluorescens, Pseudomonas oleoverans, Pseudomonas paucimobilis, Pseudomonas putida; Proteus* sp. including *Proteus morganella; Proteus*-Prov sp.; *Salmonella* sp.; *Sarcina* sp.; *Serratia* sp. including *Serratia marscens; Shigella* sp.; *Sphaerotilus* sp.; *Staphylococcus* sp. including *Staphylococcus aureus; Streptococcus* sp.; *Thiobacillus* sp.; *Xanthomonas* sp.

Fungi which can be treated with the compositions of the invention include the following. *Alternaria* sp.; *Amorphotheca* sp.; *Aspergillus niger, Aureobasidium* sp.; *Cephalosporium* sp.; *Chaetomium globosum, Cladosporium* sp.; *Fungi imperfecti; Fusarium* sp.; *Geotricum* sp.; *Gloeophyllum* sp.; *Lentinus* sp.; *Mucro* sp.; *Penicillium* sp.; *Phoma* sp.; *Rhizopus* sp.; *Saccharomyces* sp.; *Trichoderma* sp.; *Tricophyton* sp.; *Trichosporon* sp.

Algae which can be treated with the compositions of the invention include the following. *Anabaena* sp.; *Anacystis* sp.; *Ankistrodesmus* sp.; *Ascomycetes; Basidomycetes; Chlorella* sp.; *Calothrix* sp.; *Chlorococcum* sp.; *Coccomyxa* sp.; *Microcystis* sp.; *Nostoc* sp.; *Oscillatoria* sp.; *Pleurococcus; Phormidium* sp.; *Phordium luridum; Scenedesmus* sp.; *Schizothrix* sp.; *Selenastrum* sp.; *Spirogyra* sp.; *Ulothrix* sp.

Yeast which can be treated with the compositions of the invention include the following. *Candida* sp.; *Rhodotorula* sp.; *Saccharomyces* sp.

It will be readily appreciated that microbes exist in their natural environment (most often in a biofilm habitat) in a wide range of conditions and temperatures. For instance, *Bacillus licheniformis* (to name but one) is often found, inter alia, in soil environments, and can grow on the feathers of ground-dwelling and aquatic-dwelling bird species. Consequently, the biofilm-modifying nucleases of microbes must necessarily be able to perform their biological function in a correspondingly wide range of environmental conditions and temperatures, and, furthermore, such nucleases must be adapted to perform within the relatively restrictive environment of the biofilm itself. As such, the anti-biofouling compositions of the invention are similarly expected to be resistant to fluctuations in operating conditions and will thus find utility across a wide spectrum of different applications and in combination with a wide range of excipients, provided such excipients are biologically compatible which can be readily assessed by routine methods.

As described above for medical applications, the extent of the disruption of the biofilm in anti-biofouling applications may be modulated, as required, by the dose of the microbial deoxyribonuclease component of the composition. Furthermore, the dose of the microbial deoxyribonuclease component will be dependent upon the particular application and can be assessed by routine methods.

As also described above for medical applications, any of the microbial deoxyribonucleases (or any combinations thereof) of the anti-biofouling compositions described herein can be coated onto or attached to a surface susceptible to biofilm formation so as to prevent the said formation. Surface derivatization and attachment chemistries are well known in the art, as described above, and the skilled person can readily assess the suitability of surfaces for such attachment.

Microbial nucleases can be expressed by recombinant means and purified for use in compositions.

Polynucleotides encoding microbial deoxyribonucleases can be inserted into any appropriate expression vector known in the art. The term expression vector refers to a genetic construct such as a plasmid, virus or other vehicle known in the art that can be engineered to contain a polynucleotide encoding a microbial nuclease. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various appropriate promoters, including inducible and constitutive promoters, known in the art can be employed.

Transformation or transfection of a host cell with a polynucleotide can be carried out using conventional techniques well known to those skilled in the art. For example, DNA uptake can be facilitated using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Naked DNA could be used (e.g., naked plasmid DNA). Introduction of a construct comprising a microbial nuclease-encoding polynucleotide into the host cell can be effected by calcium phosphate transfection, DEAE-Dextran mediated transfection, or electroporation (Davis, L. et al. 1986. Basic Methods in Molecular Biology). One such protocol for expression of microbial nucleases involves *Bacillus subtilis* and is described in the Examples below.

Any of various art-known methods for protein purification can be used to isolate the expressed microbial nucleases. For example, preparative chromatographic separations and immunological separations (such as those employing monoclonal or polyclonal antibodies) can be used. Carrier peptides can facilitate isolation of fusion proteins that include microbial nucleases. Purification tags can be operably linked to a microbial nucleases polypeptide. For example, glutathione-S-transferase (GST) allows purification with a glutathione agarose affinity column. When either Protein A or the ZZ domain from Staphylococcus aureus is used as the tag, purification can be accomplished in a single step using an IgG-SEPHAROSE affinity column. Purification tags can subsequently be removed. Furthermore, monoclonal or polyclonal antibodies that specifically bind the microbial nuclease polypeptides can be used in conventional purification methods. Techniques for producing such antibodies are well known in the art.

Industrial scale production of proteins can be achieved by routine methods known in the art such as fermentation and the like. Common host cells used for such production include *E. coli, B. subtilis* and *S cerevisiae*.

EXAMPLES

The environmental isolate of *Bacillus licheniformis* (EI-34-6), which was isolated from the surface of the marine algae Palmaria *palmata*, is known to produce the specific secondary metabolites bacitracin and pulcherrimin when grown in an AMS bioreactor (Yan et al. 2003. Applied and Environmental Microbiology 69: 3719-3727; Nijland et al 2009, submitted). The bacteria were grown on semi-permeable membranes within the bioreactor allowing the formation of a biofilm at the air-solid interface. The antibiotic compounds were released into the media below the membranes using this particular bioreactor, but not when grown planktonically in standard shake flasks (Yan et al. 2003. Applied and Environmental Microbiology 69: 3719-3727).

When this strain was grown in the AMS bioreactor it also produced an unknown compound(s) capable of dispersing bacterial biofilms of several gram positive and gram negative bacteria. The current inventors found that when this antibiotic media from Bacillus licheniformis strain EI-34-6 was added to the medium where a target microbial biofilm was growing, it induced a physiological response in the target bacterial strain that led to disruption of the target strain from their biofilms. This disruption phenomenon was found to occur in biofilms arising from gram negative target bacterial strains but also, surprisingly, in gram positive target bacterial strains (i.e. Bacillus subtilis, Bacillus licheniformis, Micrococcus sp., Pseudomonas sp., E. coli and several unknown marine isolates).

Following a bioassay guided fractionation and LC-MS-MS peptide mass fingerprinting, two specific compounds responsible for the biofilm disruption activity were identified. These compounds were shown to be a secreted DNase (NucB) and a secreted RNase (Barnase) leading to the realisation that microbes can actively modify the biofilm by digestion of extracellular DNA and RNA components of biofilm using endogenous nuclease enzymes.

Example 1

Screening for Biofilm Disruption Activity Aided by Bioassay-Guided Fractionation Supernatant fractions having biofilm disruption activity were identified as described below.

B. licheniformis strain EI-34-6 was grown for 7 days in an AMS bioreactor as described previously (Yan et al. 2003. Applied and Environmental Microbiology 69: 3719-3727) in NGF medium (Nutrient broth (Oxoid) 13 g/l, 1% glycerol, 1 mM $FeCl_2$). The growth medium underneath the filter membrane was collected, centrifuged at 7800 rpm for 10 minutes and filtered using a 0.25 µM syringe filter to ensure sterility.

The proteins in the resulting sterile filtrate (AMS supernatant) were concentrated 50 fold upon precipitation with TCA (Sigma, UK) as follows. 100% TCA solution was added to a final concentration of 15% and the mixture was kept on ice for 30 minutes before spinning down the precipitated proteins for 10 minutes at 7800 rpm in 50 ml Falcon tubes. The pellets were washed twice using ice cold 96% ethanol, and air dried for 30 minutes at 45° C. The pellet was dissolved in 1:50th of the original volume with 0.05M Tris-HCL buffer (pH 7.0).

The concentrate was fractionated using a SUPEROSE 12 (GE Healthcare Life Sciences) gel filtration column (height 40cm, diameter 3 cm) using ultra pure water as the carrying medium and fractions of 12ml each were collected.

The resulting fractions from this step were then tested for biofilm disruption activity in a 96 well microtitre plate setup, using crude B. licheniformis strain EI-34-6 AMS supernatant as the positive control and $H_2O$ as the negative control. The activity assay is described as follows.

Biofilm disruption activity was assayed using clear 96 well flat bottom polystyrene tissue culture plates (BD-Falcon, USA). Bacillus licheniformis strain DSM13 was grown for 48-96 h in LB medium (VWR, UK) at 37° C. in a shaking incubator and diluted 1:100 in fresh LB. 200 µl of this culture was added to every well of a 96 well plate, and the plate was incubated at 37° C. for 20-28 h to allow development of the biofilm as a ring on the liquid-air interface. Biofilm disruption compounds were added in varying concentrations and the plate was further incubated for 1 hour at 37° C. All non-attached cells were removed by rinsing the plate 4 times in a container containing tap water. Attached biofilms were stained by addition of 250 µl of crystal violet (CV) to each well of the plate for 10 minutes. The CV was removed by pipetting and the plate was rinsed again in a container containing tap water until no further CV was observed to dissolve in the water. The plates were dried and 250 µl of 96% ethanol containing 2% acetic acid was added to each well. Adsorption at 595 nm was measured using a Fluostar optima plate reader (BMG labtech, UK), and the data was analysed using the MARS software package (BMG labtech, UK) and Microsoft Excel.

Proteins in the active fraction were concentrated again upon TCA precipitation and analysed by SDS page.

The fraction from the SUPEROSE 12 gel filtration fractionation which showed activity in the biofilm dispersing assay was concentrated 10× in 50mM Tris-HCL solution and separated on a native PAGE gel (Invitrogen, UK). The gel was cut in 5 pieces, broken in to small fragments by passing it trough a syringe as described, and the proteins were allowed to diffuse from the gel for 1h at RT. The liquid fraction was collected and added to established biofilms as described above for activity testing.

Biofilm disruption activity in SUPEROSE 12 gel filtration fractionation samples is shown in FIG. 1.

Example 2

Identification of Specific Proteins in a Biofilm Disrupting Fraction by Peptide Mass Fingerprinting After the fractionation, purification and bioassay steps noted above, three proteins bands were identified on the gel corresponding to the active fraction as described in more detail below.

Figure 2:
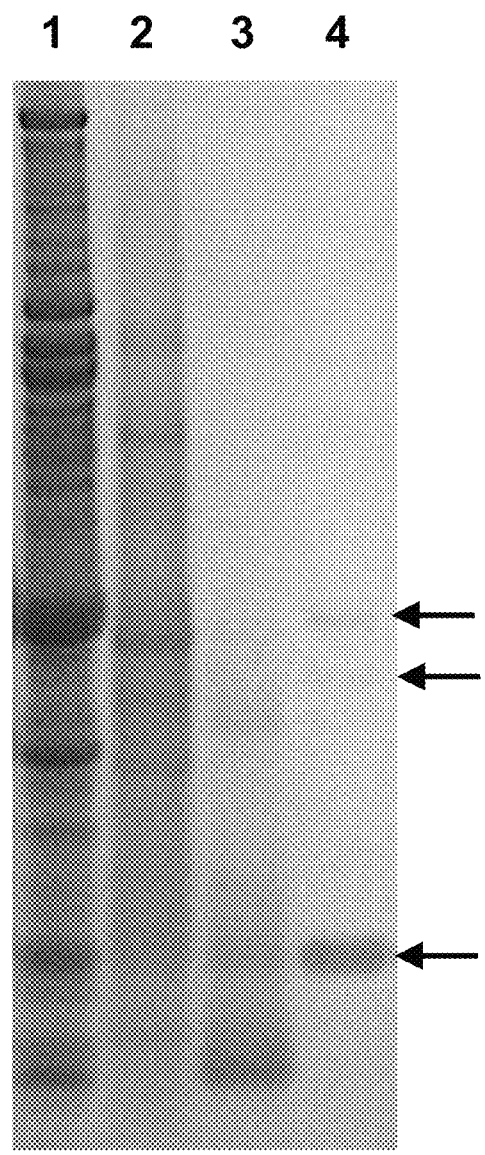
FIG. 2 shows a COOMASSIE-stained Tris-Tricene gel of *B. licheniformis* strain EI-34-6 crude AMS supernatant (lane 1) and concentrated SUPEROSE 12 fractions (lanes 2, 3 & 4). The 12, 30 and 36 kDa bands subjected to peptide mass fingerprinting are highlighted (lane 4).

The fraction from the SUPEROSE 12 (GE Healthcare Life Sciences) gel filtration having biofilm disruption activity was concentrated 10× upon TCA precipitation as described previously (Nijland R, Lindner C, van Hartskamp M, Hamoen LW, Kuipers. OP 2007. J Biotechnol. 127(3): 361-72.) and separated on a 4-12% Tris-Tricine gel using IVIES buffer (Invitrogen, UK). A Novex Sharp Prestained protein standard (Invitrogen, UK) was also loaded to determine protein size. After electrophoresis, the gel was stained using BIOSAFE COOMASSIE (Biorad, UK) according to the manufacturer's protocol. Three bands were visible on the gel, 1 abundant band at 12kD and two higher bands around 30 and 36kD (see FIG. 2).

These three bands were analysed by LCMS following in-gel tryptic digest as follows. The excised gel piece was put into a small volume of $NH_4HCO_3$ pH 7.8 and mashed to small pieces. The gel pieces were washed with 60% acetonitrile and washed with $NH_4HCO_3$ pH 7.8 prior to reduction in 50 µl of 10 mM DTT in 100 mM $NH_4HCO_3$ for 1 h at 56° C. Subsequently, cysteines were alkylated by adding 50 µl of freshly prepared 50 mM iodoacetamide in 100 mM $NH_4HCO_3$ and incubating in the dark at room temperature for 30 min. Gel pieces were repeatedly washed with 100 mM $NH_4HCO_3$ and 50% acetonitrile, dehydrated using 70 µl of 100% acetonitrile. Proteins were in gel digested with 8 ng of trypsin (Promega) in 50 mM $NH_4HCO_3$, 1 mM $CaCl_2$ and incubation overnight, shaking in a thermomixer at 37° C. The digest was stopped through addition of 5% of TFA and the solution containing peptides was transferred to a new tube. The gel pieces were washed twice with 60% acetonitrile containing 2% TFA and the washes were pooled with the aqueous supernatant after the digest. The volume of the digests was reduced to 10 µl in a speedvac and 1 µl of this was analysed by LCMSMS.

Peptides were concentrated on a PEPMAP C-18 trap column (300 µm ID×5mm) and separated on a Pepmap PEPMAP C18 reversed phase column (Dionex, UK) (3 µm particles, 75 µm ID×250 mm) using a linear gradient over 42 min from 96% A (0.05% formic acid), 4% B (0.05% formic acid, 80% acetonitrile) to 35% A, 65% B and a flow rate of 300nl/min.

The spray voltage was 1.6 kV and the temperature of the heated capillary was set to 200° C. Survey scans were acquired with enabled lockmass from 400-1600 Da at a resolution of 30,000 at m/z 400 after accumulation of 5×105 ions. The 10 most intense ions of the survey scan were sequenced concurrently to full scan acquisition in the orbitrap by collision-induced dissociation (CID, normalised collision energy 35%) in the LTQ. Maximum filling times were 50 ms for the full scans and 100 ms for the MSMS scans. Precursor ion charge state screening was enabled and unassigned charge states and singly charged ions were rejected. Dynamic exclusion was enabled for 180 s with a maximum dynamic exclusion list of 50 entries and a relative mass window from −0.5 Da to +1 Da.

Raw data were transformed into peak lists in the mascot generic file format (*.mgf) using PROTEINEXPLORER version 1.0 and default settings. Mgf files were submitted to the X! TANDEM search engine using the gpm interface (www.thegpm.org) and the following parameters: tryptic digestion with up to one missed cleavage site, precursor ion tolerance ±20 ppm, product ion tolerance 0.6 Da, carboxamidomethylation of Cys as a fixed modification and Oxidation of Met as a variable modifications. The following additional variable modifications were considered in two refinement stages: phosphorylation of Ser, Thr and Tyr, oxidation of Met and Trp, methylation of Cys, Asp, Glu, His, Lys and Arg and deamidation of Asn and Gln in the first refinement stage and di-oxidation of Met and Trp, dehydration of Ser and Thr, lack of carboxamidomethylation of Cys, methylation of Asn and Gln, carboxamidomethylation of Lys, His, Glu and Asp in the second refinement stage. The following databases were searched: NCBI NC 006270.faa 2008.04.22 (Bacillus_licheniformis_ATCC_14580), NCBI NC_006322.faa 2008.04.22(Bacillus_licheniformis_DSM_13), NCBI NC 000964.faa 2008.04.22 (Bacillus_subtilis) and the common repository for adventitious proteins (cRAP) version 2009.05.01.

The lowest band, cut out at approximately 12 kD, contained two small proteins, both of them nucleases. The most abundant protein was Barnase (locus_tag: BL03601), a secreted ribonuclease, and the other protein was NucB (locus_tag: BL00126), a secreted deoxyribonuclease.

The second band, cut out at approximately 30 kD, contained three different proteins. The most abundant protein was protein YckK (locus_tag: BL01829) from the solute-binding family. Also present was the glycine betaine ABC transporter (opuAC; locus_tag: "BL01556") and the ribonuclease present in the 12 kD band. The third band, cut out at approximately 36 kD contained three different proteins. The most abundant protein was again the glycine betaine ABC transporter. Also present was an ABC transport system substrate-binding protein and probably also the putative extracellular solute-binding protein YckB (locus_tag: BL01818).

Based on these results the two most likely candidates to have biofilm disruption activity were Barnase and NucB. NucB was chosen for further analysis.

Example 3

Cloning and Over Expression of B. licheniformis NucB in Bacillus subtilis NZ8900

Primers were designed to amplify the NucB nuclease gene based on the published genome sequence of B. licheniformis DSM13 (ATCC14580) (Rey et al. 2004. Genome Biology, 5 (10)).

Primers were designed to amplify the nucB gene from the chromosomal DNA of Bacillus licheniformis EI-34-6 based on the sequence known for strain DSM13 (GenBank: AE017333.1) (See Table 1 below).

Figure 3:
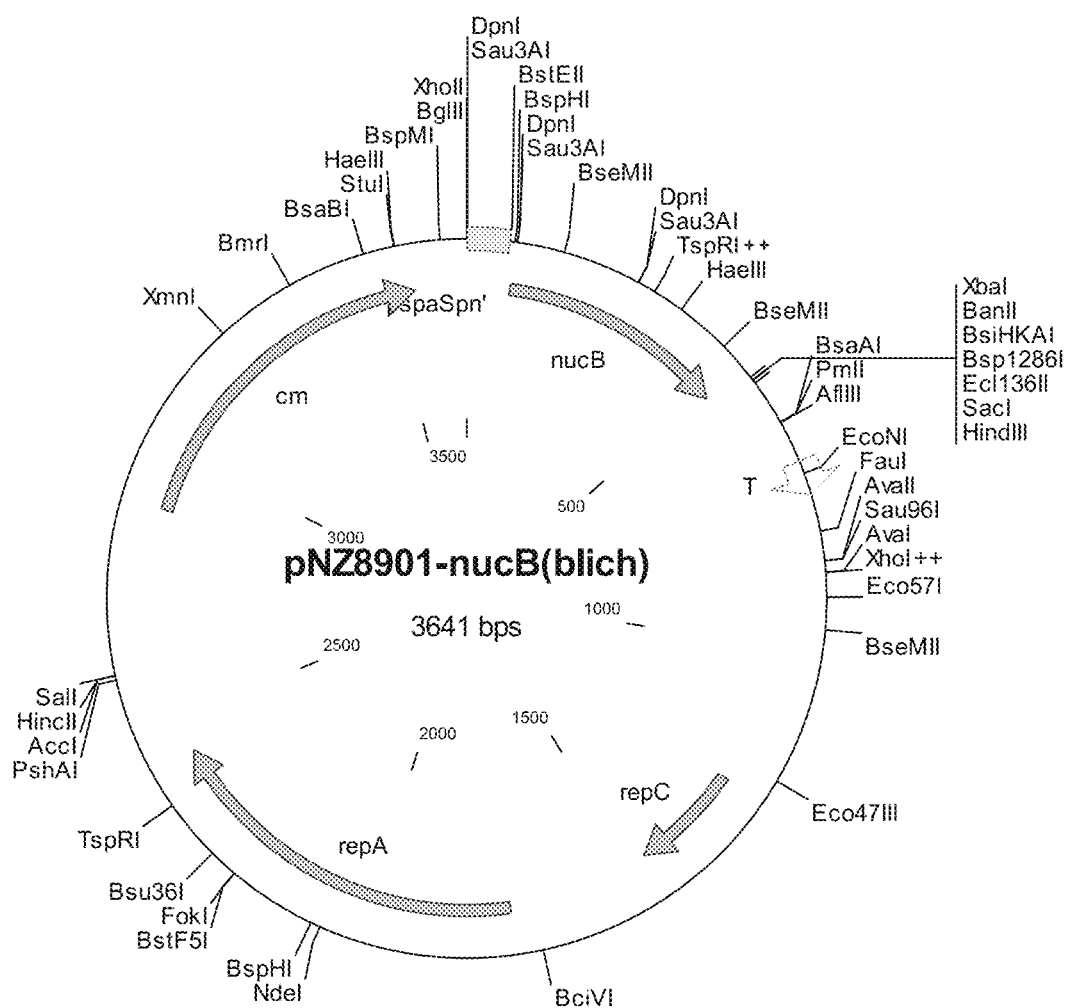
FIG. 3 shows a map of plasmid containing polynucleotide sequences of the *B. licheniformis* strain EI-34-6 NucB nuclease gene.

The nucB gene was successfully amplified from B. licheniformis EI-34-6 chromosomal DNA and cloned into the SURE expression vector pNZ8901 (see FIG. 3) using E. coli as intermediate host as described below.

The reaction to amplify nucB did not yield a single band, but a faint band was present at the correct size. This band was isolated from the agarose gel (Invitrogen gel isolation kit) and used as a template for a new PCR.

The amplified gene was digested using Eco91I, XbaI (nucB) and ligated into a likewise digested vector pNZ8901 (CmR). The ligation mixture was transformed to E. coli MC1061 using the $CaCl_2$ as described before (Sambrook, J., E. F. Fritsch, and T. Maniatis. 1989. Molecular cloning: A Laboratory Manual. Cold Spring Harbour Laboratory Cold Spring Harbour, NY). Colonies were screened using colony PCR with the unique primers mentioned above and plasmids were isolated from positive clones. Plasmids were analysed by restriction digestion and correct plasmids were sequenced.

The constructed plasmid was transformed to Bacillus subtilis NZ8900 (Bongers R S, Veening J W, Van Wieringen M, Kuipers O P, Kleerebezem M. 2005. Appl. Environ Microbiol. 71(12): 8818-24) using natural competence as described before (Spizizen J. 1958. Proceedings of the National Academy of Sciences of the United States of America 44: 1072-1078).

The vector could be successfully transformed to het SURE expression strain B. subtilis NZ8900.

Correct B. subtilis NZ8900+pNZ8901/2-nucB clones were screened on DNase test agar containing methyl Green (Oxoid) as follows. A colony was streaked onto the DNase test agar and grown O/N at 30° C. The next morning a drop of B. subtilis ATCC6633 culture supernatant inducer in 1% agar was spotted next to the colony. The plates were further incubated for 2 h at 37° C. and colonies developing a halo due to the degradation of DNA were judged positive and transferred to a shakeflask containing LB and the appropriate antibiotics (Kanamycin and Chloramphenicor/Erythromicin). At an $OD_{600}$ of ~1.0 10% ATCC6633 supernatant was added to induce expression and the total culture supernatant was harvested 2 hours after induction. Overproduction of the NucB was visualised on SDS-page after 10× concentration upon TCA precipitation as described above.

Example 4

Sequencing of the B. licheniformis EI-34-6 nucB Gene

After successful amplification of nucB from the chromosome of B. licheniformis EI-34-6, as described above, the gene was sequenced to identify potential differences with the sequenced strain (DSM13). nucB (22 bp of total 428 bp=5.1%) contained base pair substitutions, leading to 4 amino acid changes in the NucB protein (see FIG. 4).

Example 5

Testing of Heterologously Overproduced NucB for DNase and Biofilm Disruption Activities The supernatant of B. subtilis NZ8900 containing the induced over-expression construct of nucB (as described in Example 3) was tested for its capability for dispersing established biofilms in the biofilm disruption assay described in Example 1. The supernatant was capable of dispersing functional biofilms at concentrations down to 3 ng/ml. The concentration of nucB protein present in the supernatant was quantified following separation of proteins by SDS-PAGE and visualisation using standard methods.

Figure 5:
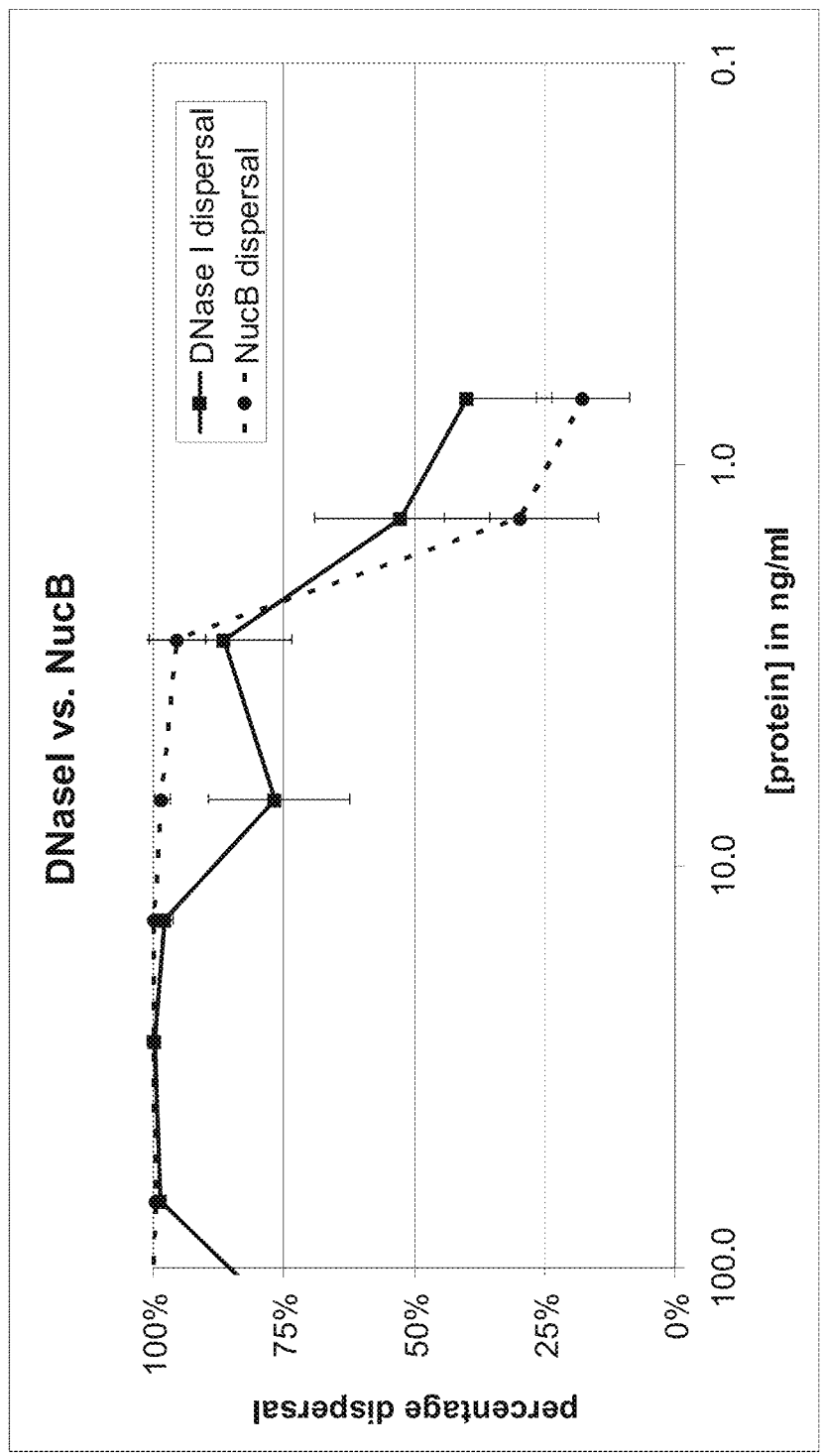
FIG. 5 shows a comparison of biofilm disruption as between *B. licheniformis* strain EI-34-6 nucB AMS supernatant and purified DNaseI from bovine pancreas.

In a disruption assay the efficiency of disruption of NucB and commercially obtained bovine DNaseI were compared. Based on this test it was shown that NucB has the capability to completely disperse an established biofilm at a 5 fold lower concentration (w/v) than the DNaseI. For example, 100% biofilm disruption could be observed with DNaseI only at concentrations of 15 ng/ml and higher. In contrast, however, 100% biofilm disruption activity could be observed with NucB at concentrations as low as 3 ng/ml (see FIG. 5).

DNase activity was tested by incubating purified plasmid DNA with the DNase containing fractions for 30 minutes at 37° C. The samples were loaded on an agarose gel to visualize DNA degradation.

The AMS supernatant of B. licheniformis EI-34-6 was tested for dispersal of biofilms growing on several surfaces. In all conditions tested the AMS supernatant was capable of removing bacterial biofilm. The surfaces tested include plastic (polystyrene 96 and 24 well microtiter plates), glass (borosilicate glass bottles and glass microscope slides) and steel (coupons and pins of stainless steel).

The activity of the biofilm dispersing nucleases was tested, when diluted to a maximum of 1000 fold, in either demineralised water, LB growth medium, DNAse I reaction buffer containing magnesium chloride and calcium chloride (Fermentas), and mixtures of the above. In all conditions, biofilm dispersal activity was found.

BENZONASE was also tested for biofilm disruption activity and was found also to be highly effective. BENZONASE is a genetically engineered nuclease with deoxyribonuclease activity derived from Serratia marcescens, a gram-negative bacterium of the family Enterobacteriaceae.

Example 6

Visualisation of NucB Biofilm Disruption Activity

Biofilms with extracellular polymeric substances (EPS) matrix were tested for NucB biofilm disruption activity.

Figure 11:
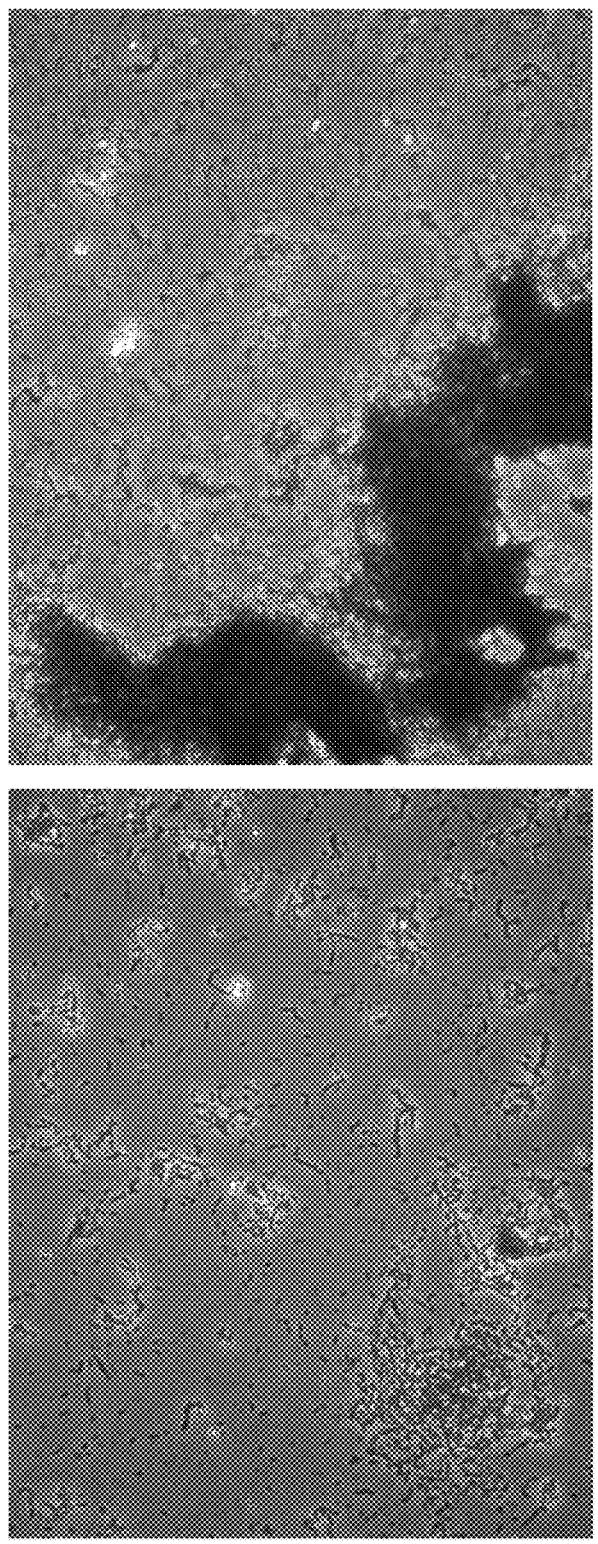
FIG. 11 shows phase contrast micrographs of untreated (top panel) and NucB-treated (bottom panel) *Pseudomonas* biofilm.

EPS matrix Pseudomonas biofilms were exposed to purified NucB enzyme used at 3 ng/ml. After one hour phase contrast images were taken using 40× magnification (Leica). Images are presented at FIG. 11 showing the effect of NucB on biofilm dispersal (bottom panel) as compared to untreated samples (top panel).

Example 7

Effect of NucB Biofilm Disruption Activity on a Range of Microbial Biofilms

Various microbial biofilms were tested for NucB biofilm disruption activity.

Biofilms derived from a range of microbes (Pseudomonas sp., Vibrio sp., B. Licheniformis DSM13, Arthrobacter sp., Pseudoalteromonas sp., Psychrobacter sp. and yeast) were exposed to purified NucB enzyme used at 3 ng/ml. Biofilm dispersal activity was measured after one hour.

Figure 12:
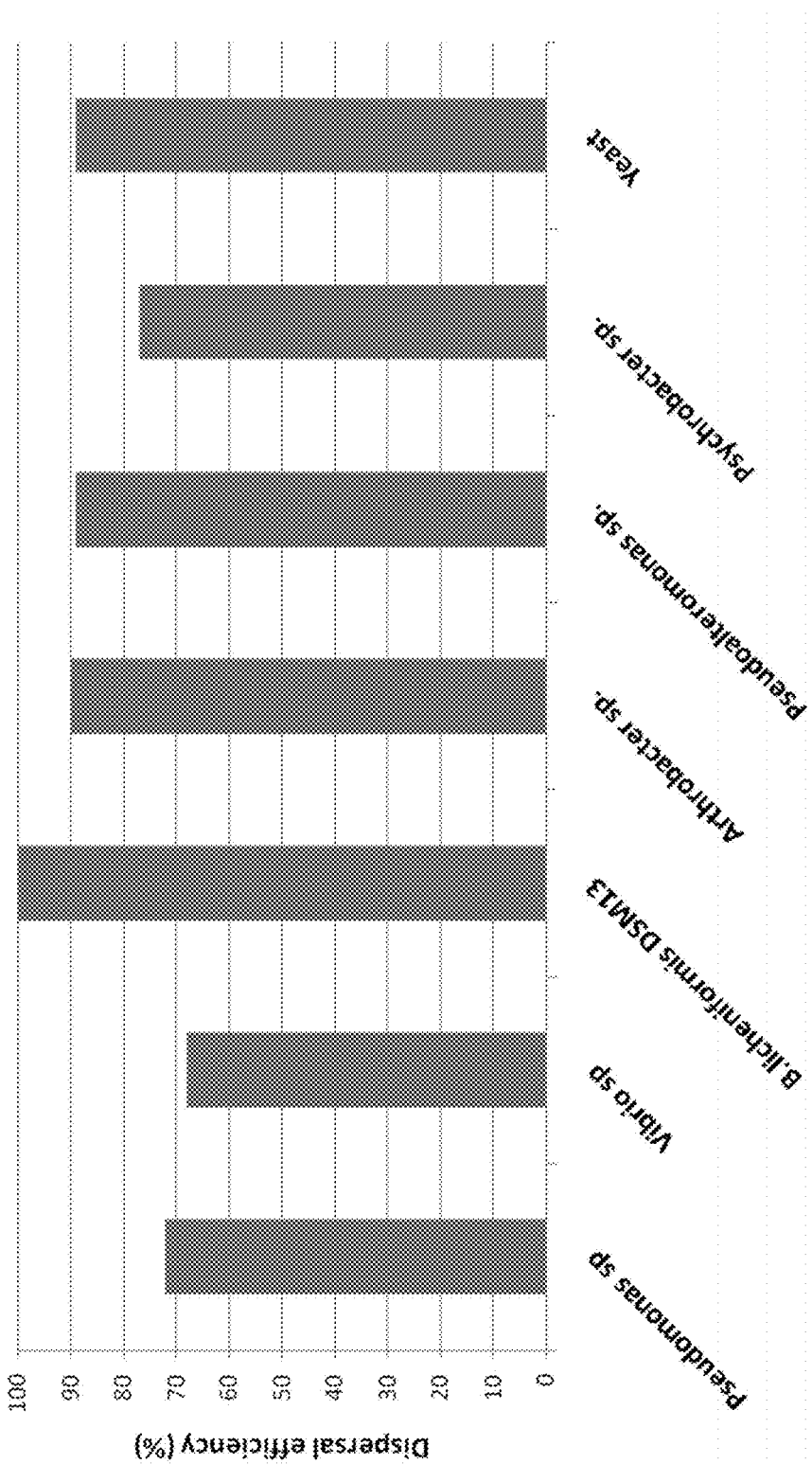
FIG. 12 shows the effect of NucB treatment on various microbial (bacterial and yeast) biofilms.

As demonstrated in FIG. 12, a deoxyribunuclease from one microbial species has excellent biofilm dispersal activity against biofilms derived from a range of other disparate microbes.

Example 8

Effect of NucB Biofilm Disruption Activity on a Contact Lens Surface

The ability of NucB to disperse a mixed natural biofilm from the surface of a contact lens was tested.

A mixed natural biofilm established on the surface of a contact lens structure was exposed to purified NucB enzyme used at 3 ng/ml. Biofilm dispersal activity was measured after one hour.

Figure 13:
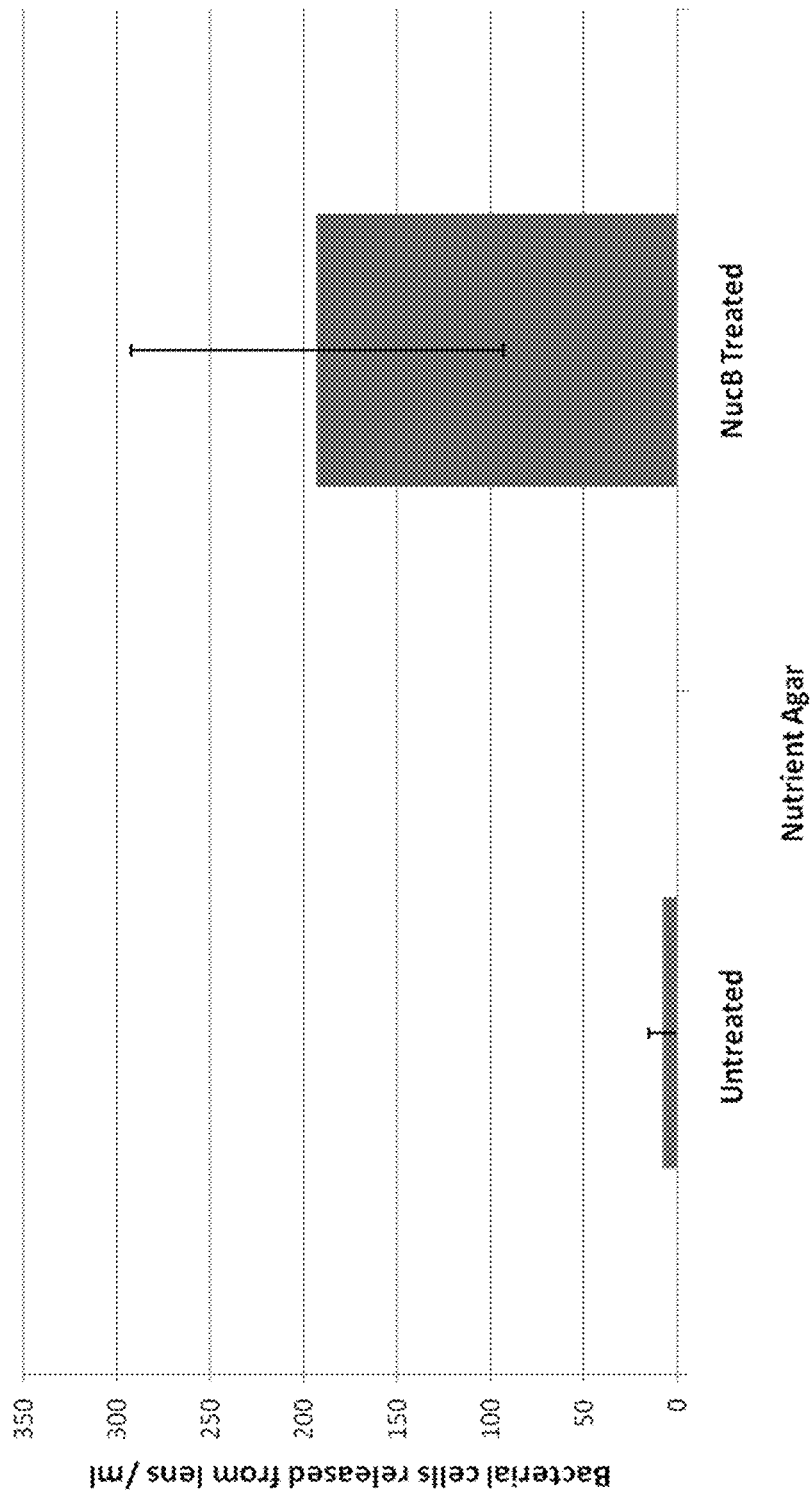
FIG. 13 shows the effect of NucB treatment on fouled contact lenses.

As shown in FIG. 13, NucB possesses excellent biofilm dispersal activity against a fouled contact lens surface. An increase in bacteria per ml released from the lens indicates nuclease breakdown of the biofilm on the lens.

TABLE 1

Primer sequence used to amplify the nucB gene from the chromosomal DNA of Bacillus licheniformis EI-34-6 based on the sequence known for strain DSM13.

| Primer description | Primer sequence (5' to 3') | SEQ ID No. |
| --- | --- | --- |
| nucB-forward primer + BsteII restriction site. | ATAGGTGACCGTCATGATCAAAAAATGGGC GGTTCATCTGC | 6 |
| nucB-reverse primer + XbaI restriction site. | ATCTCTAGATATTTGTTTTTCGCCTTTTATTG | 7 |

While this invention has been particularly shown and described with references to preferred embodiments thereof, it will be understood by those skilled in the art that various

What is claimed is:

1. A pharmaceutical or anti-biofouling composition for disrupting a biofilm or preventing biofilm formation comprising an isolated microbial deoxyribonuclease polypeptide and an excipient, wherein said composition is coated on at least a portion of a patient-contactable surface of an indwelling medical device, and wherein the microbial deoxyribonuclease is as set forth in SEQ ID NO. 4.

2. The composition of claim 1 further comprising an antimicrobial compound.

3. The composition of claim 2 wherein the antimicrobial compound is an antiparasitic compound which is one or more of a benzazole; a macrocycle; pyrantel pamoate; diethylcarbamazine; niclosamide; praziquantel; melarsoprol; and eflornithine.

4. The composition of claim 2 wherein the antimicrobial compound is an antiviral compound which is one or more of a nucleoside analog reverse transcriptase inhibitor; an uncoating inhibitor; a protease inhibitor; zanamivir; oseltamivir; and rifampin.

5. The composition of claim 2 wherein the antimicrobial compound is an antibacterial compound which is one or more of an aminoglycoside; a beta-lactam; a cephalosporin; a quinolone; a macrolide; an oxazolidinone; an ansamycin; a sulphonamide; a tetracycline; a glycopeptide; sulfisoxazole, trimethoprim, novobiocin, daptomycin and linezolid.

6. The composition of claim 2 wherein the antimicrobial compound is an antifungal compound which is one or more of an azole, a macrocycle, an allyl amine, an echinocandin, polygodial, ciclopyrox, tolnaftate, benzoic acid, undecylenic acid, flucytosine and griseofulvin.

7. The composition of claim 2 wherein the composition is an anti-biofouling composition and the antimicrobial compound is an antibacterial compound which is a parahydroxy benzoic acid ester (parabens).

8. A method of preventing or disrupting a biofilm on a surface comprising contacting the surface with an effective dose of the composition of claim 1, wherein the surface is at least a portion of a patient-contactable surface of an indwelling medical device.

9. The method of claim 8 wherein said surface is a surface of a catheter.

10. The method of claim 8 wherein the microbial deoxyribonuclease of said composition is attached to said surface.

11. The composition of claim 1 wherein said device is a catheter.

12. A method of preventing or disrupting a biofilm on a surface comprising:
expressing a microbial deoxyribonuclease polypeptide from an expression vector that comprises a polynucleotide encoding the microbial deoxyribonuclease; and
contacting the surface with an effective dose of the microbial deoxyribonuclease polypeptide, wherein the surface is at least a portion of a patient-contactable surface of an indwelling medical device, wherein the microbial deoxyribonuclease is as set forth in SEQ ID NO: 4.

13. The composition of claim 1 wherein said composition is attached to said at least a portion of the patient-contactable surface of said device.

14. The composition of claim 2 wherein said antimicrobial compound is an antibacterial compound, an antiparasitic compound, an antifungal compound or an antiviral compound.

15. The composition of claim 3 wherein:
said benzazole is albendazole, mebendazole or tiabendazole; or
said azole is metronidazole or tinidazole; or
said macrocycle is amphotericin B, rifampin or ivermectin.

16. The composition of claim 4 wherein:
said nucleoside analog reverse transcriptase inhibitor is acyclovir, didanosine, stavudine, zidovudine, lamivudine, abacavir, emtricitabine or entecavir; or
said uncoating inhibitor is amantadine, rimantadine or pleconaril; or
said protease inhibitor is saquinavir, ritonavir, indinavir, nelfinavir or amprenavir.

17. The composition of claim 5 wherein:
said aminoglycoside is gentamicin, kanamycin or streptomycin; or
said beta-lactam is penicillin, ampicillin or imipenem; or
said cephalosporin is ceftazidime, or
said quinolone is ciprofloxacin; or
said macrolide is azithromycin, clarithromycin, dirithromycin, erythromycin, roxithromycin or telithromycin; or
said oxazolidinone is linezolid; or
said ansamycin is rifamycin; or
said tetracycline is doxycycline; or
said glycopeptide is vancomycin.

18. The composition of claim 6 wherein:
said azole is miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole or abafungin; or
said macrocycle is natamycin, rimocidin, filipin, nystatin, amphotericin B, candicin or hamycin; or
said allyl amine is terbinafine, naftifine or butenafine; or said echinocandin is andidulafungin, caspofungin or micafungin.

19. The composition of claim 7 wherein said parahydroxy benzoic acid ester is methyl-paraben, ethyl-paraben, propyl-paraben, butyl-paraben or benzyl-paraben.

20. The method of claim 8 wherein said surface is a surface of a central venous catheter, intravascular catheter, urinary catheter, Hickman catheter, peritoneal dialysis catheter, endrotracheal catheter, or the surface of a mechanical heart valve, a cardiac pacemaker, an arteriovenous shunt, a schleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.

21. The composition of claim 1 wherein said device is a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a schleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.

* * * * *